United States Patent
De Beule et al.

(10) Patent No.: US 12,186,021 B2
(45) Date of Patent: Jan. 7, 2025

(54) METHOD AND SYSTEM FOR PATIENT-SPECIFIC VIRTUAL PERCUTANEOUS STRUCTURAL HEART INTERVENTION

(71) Applicant: FEops NV, Ghent (BE)

(72) Inventors: Matthieu Robert Anna Firmin De Beule, Ghent (BE); Peter Eddy J. Mortier, Ingooigem (BE); Patricio Javier Astudillo, Ghent (BE); Nic Debusschere, Ghent (BE)

(73) Assignee: FEops NV, Ghent (BE)

( * ) Notice: Subject to any disclaimer, the term of this patent is extended or adjusted under 35 U.S.C. 154(b) by 1063 days.

(21) Appl. No.: 16/982,526

(22) PCT Filed: Mar. 8, 2019

(86) PCT No.: PCT/EP2019/055907
§ 371 (c)(1),
(2) Date: Sep. 18, 2020

(87) PCT Pub. No.: WO2019/179793
PCT Pub. Date: Sep. 26, 2019

(65) Prior Publication Data
US 2021/0022806 A1    Jan. 28, 2021

(30) Foreign Application Priority Data
Mar. 23, 2018 (EP) ..................... 18163655

(51) Int. Cl.
*A61B 34/10*    (2016.01)
*A61F 2/24*     (2006.01)

(52) U.S. Cl.
CPC ............ *A61B 34/10* (2016.02); *A61F 2/2412* (2013.01); *A61B 2034/104* (2016.02);
(Continued)

(58) Field of Classification Search
CPC .............. A61B 34/10; A61B 2034/104; A61B 2034/105; A61B 2034/108;
(Continued)

(56) References Cited

U.S. PATENT DOCUMENTS 8,315,812 B2   11/2012  Taylor
8,548,778 B1   10/2013  Hart et al.
(Continued)

FOREIGN PATENT DOCUMENTS

CN    106037931 A  * 10/2016  ........... A61B 5/1076
DE    102012205504 A1  10/2013
(Continued)

OTHER PUBLICATIONS

European Search Report dated Jul. 11, 2017 in EP Patent Appl. Serial No. 17154648.4.
(Continued)

*Primary Examiner* — Jose L Couso
(74) *Attorney, Agent, or Firm* — Greenberg Traurig, LLP; Christopher C. Bolten; Robert D. Ward

(57) ABSTRACT

A system and method for selecting, from a series of cardiac implants having different sizes, the cardiac implant having optimum size for implantation in a patient. The method includes obtaining data representative of a patient-specific cardiac region and predicting the optimum size of the cardiac implant best matching a predefined criterion when deployed in the cardiac region. The predicting includes querying a database; determining parameter values for a parametric model representation of the patient-specific cardiac region; and/or entering the data representative of the patient-specific cardiac region into an artificial intelligence device.

15 Claims, 7 Drawing Sheets

(52) U.S. Cl.
CPC ... *A61B 2034/105* (2016.02); *A61B 2034/108* (2016.02); *G06T 2210/41* (2013.01)

(58) Field of Classification Search
CPC ........ A61B 2034/102; A61B 2034/107; A61B 6/504; A61B 5/02007; A61B 5/021; A61B 5/1076; A61F 2/2412; A61F 2240/002; A61F 2/2415; A61F 2/2427; A61F 2/2496; A61F 2/24; G06T 2210/41; G06T 7/0012; G06T 2207/30048; G06T 2207/30101; G06T 19/00; G06T 2200/04; G06T 17/00; G06T 2207/30104; G06T 2207/30004; G06T 11/00; G06T 19/20; G06T 13/20; G06T 15/00; G06T 2207/10076; G06T 2207/30252; G06T 7/251; G06T 3/4046; G06T 5/60; G06T 9/002; G06T 2207/20076; G06T 2207/20081; G06T 2207/20084; G06V 10/20; G06V 20/52; G06V 20/64; G06V 2201/031; G06V 40/10; G06V 10/454; G06V 10/54; G06V 10/774; G06V 10/82; G06V 30/18057; H04N 23/611; H04N 23/67; G06N 3/02; G06N 3/08–088; G06N 3/0445; G06N 3/0454; G06N 3/4046; G06N 7/00; G06N 7/01; G06N 20/00; G06K 7/1482; G06F 18/214; G06F 18/22; G06F 18/241; G06F 18/2415; Y10S 128/925

See application file for complete search history.

(56) References Cited

U.S. PATENT DOCUMENTS

| | | | |
|---|---|---|---|
| 8,594,950 | B2 | 11/2013 | Taylor |
| 8,682,626 | B2 | 3/2014 | Ionasec et al. |
| 9,757,073 | B2 | 9/2017 | Goshen et al. |
| 9,805,463 | B2 | 10/2017 | Choi et al. |
| 9,839,399 | B2 | 12/2017 | Fonte et al. |
| 10,258,303 | B2 | 4/2019 | Grass et al. |
| 10,275,876 | B2 | 4/2019 | Reicher et al. |
| 10,456,094 | B2 | 10/2019 | Fonte et al. |
| 10,600,181 | B2 | 3/2020 | Petersen et al. |
| 10,695,131 | B2 | 6/2020 | Weber et al. |
| 10,789,772 | B2 | 9/2020 | Mortier et al. |
| 10,803,592 | B2 | 10/2020 | Grady et al. |
| 11,045,256 | B2 | 6/2021 | Mortier et al. |
| 11,051,885 | B2 | 7/2021 | Mortier et al. |
| 11,069,136 | B2 | 7/2021 | Mortier et al. |
| 11,238,587 | B2 | 2/2022 | Min et al. |
| 11,288,813 | B2 | 3/2022 | Grady et al. |
| 11,331,149 | B2 | 5/2022 | Mortier et al. |
| 2004/0225212 | A1 | 11/2004 | Okerlund et al. |
| 2005/0043609 | A1 | 2/2005 | Murphy et al. |
| 2007/0135707 | A1 | 6/2007 | Redel et al. |
| 2008/0319448 | A1 | 12/2008 | Lavallee et al. |
| 2009/0082660 | A1 | 3/2009 | Rahn et al. |
| 2010/0042105 | A1 | 2/2010 | Park et al. |
| 2011/0153286 | A1 | 6/2011 | Zaeuner et al. |
| 2011/0182492 | A1* | 7/2011 | Grass .................. A61B 6/5247 378/150 |
| 2012/0053466 | A1 | 3/2012 | Bianchi et al. |
| 2014/0219537 | A1 | 8/2014 | Carelsen et al. |
| 2015/0051884 | A1 | 2/2015 | Grady et al. |
| 2015/0112659 | A1 | 4/2015 | Mortier |
| 2015/0112901 | A1 | 4/2015 | Singer |
| 2015/0178938 | A1 | 6/2015 | Gorman, III et al. |
| 2015/0178939 | A1 | 6/2015 | Bradski et al. |
| 2015/0182255 | A1 | 7/2015 | Shivkumar |
| 2015/0223773 | A1 | 8/2015 | John et al. |
| 2015/0235569 | A1 | 8/2015 | Babiker et al. |
| 2015/0370995 | A1 | 12/2015 | Wakai |
| 2016/0038246 | A1 | 2/2016 | Wang et al. |
| 2016/0128786 | A1* | 5/2016 | Weber .................. G06T 19/00 382/128 |
| 2016/0166332 | A1 | 6/2016 | Wang et al. |
| 2016/0199198 | A1 | 7/2016 | Dietz et al. |
| 2016/0267673 | A1 | 9/2016 | Grbic et al. |
| 2016/0270859 | A1 | 9/2016 | Park et al. |
| 2017/0000562 | A1 | 1/2017 | Frank et al. |
| 2017/0150928 | A1 | 6/2017 | Del Alamo De Pedro et al. |
| 2017/0216026 | A1* | 8/2017 | Quill .................. A61F 2/2418 |
| 2017/0258527 | A1 | 9/2017 | Wang et al. |
| 2017/0270663 | A1 | 9/2017 | Hoffmann et al. |
| 2017/0323481 | A1 | 11/2017 | Tran et al. |
| 2017/0360510 | A1 | 12/2017 | Bischoff et al. |
| 2018/0116725 | A1 | 5/2018 | Ashikaga et al. |
| 2018/0289422 | A1 | 10/2018 | Mortier et al. |
| 2018/0289488 | A1* | 10/2018 | Orth .................... A61B 5/6853 |
| 2018/0365838 | A1 | 12/2018 | Lorenz et al. |
| 2019/0090951 | A1 | 3/2019 | Camus et al. |
| 2019/0298450 | A1 | 10/2019 | Dasi et al. |
| 2019/0357981 | A1 | 11/2019 | Mortier et al. |
| 2019/0392942 | A1 | 12/2019 | Sorenson et al. |
| 2021/0022806 | A1 | 1/2021 | De Beule et al. |
| 2021/0346097 | A1 | 11/2021 | Dasi et al. |
| 2022/0172848 | A1 | 6/2022 | De et al. |
| 2022/0273369 | A1 | 9/2022 | Mortier et al. |
| 2022/0392642 | A1 | 12/2022 | Dasi et al. |
| 2023/0119535 | A1 | 4/2023 | Michiels et al. |
| 2023/0310080 | A1 | 10/2023 | Lee et al. |

FOREIGN PATENT DOCUMENTS

| | | |
|---|---|---|
| WO | WO-2013156546 A2 | 10/2013 |
| WO | WO-2013171039 A1 | 11/2013 |
| WO | WO-2014009294 A1 | 1/2014 |
| WO | WO-2016038169 A1 | 3/2016 |
| WO | WO-2016177647 A1 | 11/2016 |
| WO | WO-2018141927 A1 | 8/2018 |
| WO | WO-2019179793 A1 | 9/2019 |
| WO | WO-2020182651 A1 | 3/2020 |
| WO | WO-2022241425 A1 | 11/2022 |
| WO | WO-2022241432 A1 | 11/2022 |
| WO | WO-2023152326 A1 | 8/2023 |

OTHER PUBLICATIONS

European Search Report dated Oct. 2, 2018 in EP Patent Appl. Serial No. 18163655.6.
Extended European Search Report dated Sep. 14, 2019 in EP Patent Appl. Serial No. 19161587.7.
International Search Report & Written Opinion dated Jun. 5, 2020 in Int'l PCT Patent Appl. Serial No. PCT/EP2020/056000.
International Search Report and Written Opinion dated Jul. 15, 2016 in Int'l PCT Patent Appl. Serial No. PCT/EP2016/059688.
International Search Report and Written Opinion dated Jul. 30, 2013 in Int'l PCT Patent Appl. Serial No. PCT/EP2013/058392.
International Search Report and Written Opinion dated Jun. 4, 2018 in Int'l PCT Patent Appl. Serial No. PCT/EP2018/052701.
International Search Report and Written Opinion dated May 31, 2019 in Int'l PCT Patent Appl. Serial No. PCT/EP2019/055907.
Mortier, et al., A Novel Simulation Strategy for Stent Insertion and Deployment in Curved Coronary Bifurcations: Comparison of Three Drug-Eluting Stents, Annals of Biomedical Engineering, vol. 38(1):88-99 (Jan. 2010).
Russ, et al., Simulation of Transcatheter Aortic Valve Implantation Under Consideration of Leaflet Calcification, 35th Annual International Conference of the IEEE EMBS, Osaka, Japan, pp. 711-714 (Jul. 2013).
Vy, et al., Review of Patient-Specific Simulations of Transcatheter Aortic Valve Implantation, HAL Archives, https:/hal-univ-rennes1. archives-ouvertes.fr/hal-01196296, pp. 1-33, (Sep. 9, 2015).
U.S. Appl. No. 14/399,781 / U.S. Pat. No. 10,789,772, filed Nov. 7, 2014 / Sep. 29, 2020.
U.S. Appl. No. 15/570,976, filed Oct. 31, 2017.
U.S. Appl. No. 16/482,509, filed Jul. 31, 2019.

(56) References Cited

OTHER PUBLICATIONS

U.S. Appl. No. 16/987,794, filed Aug. 7, 2020.
U.S. Appl. No. 17/003,653, filed Aug. 26, 2020.
Aguado, et al., In Silico Optimization of Left Atrial Appendage Occluder Implantation Using Interactive and Modeling Tools, Frontiers in Physiology, vol. 10, Article 237 (Mar. 2019).
Basri, et al., The Hemodynamic Effects of Paravalvular Leakage Using Fluid Structure Interaction; Transcatheter Aortic Valve Implantation Patient, Journal of Medical Imaging and Health Informatics, 6(5):1513-1518 (Oct. 2016).
Ghadimi, M.D., et al., Perioperative Conduction Disturbances After Transcatheter Aortic Valve Replacement, Journal of Cardiothoracic and Vascular Anesthesia, 27(6):1414-1420 (Dec. 2013).
International Search Report & Written Opinion dated Feb. 21, 2023 in Int'l PCT Patent Appl. Serial No. PCT/EP2022/0784256 (0610).
Mill, et al., Sensitivity Analysis of In Silico Fluid Simulations to Predict Thrombus Formation After Left Atrial Appendage Occlusion, Mathematics, 9(18):2304-2323 (Jan. 2021).
Morlacchi, et al., Sequential Structural and Fluid Dynamic Numerical Simulations of a Stented Bifurcated Coronary Artery, Journal of Biomechanical Engineering, vol. 133, 11 pages (Dec. 2011).
Nucifora, et al., Evaluation of the Left Atrial Appendage With Real-Time 3-Dimensional Transesophageal Echocardiography, Implications for Catheter-Based Left Atrial Appendage Closure, Circulation: Cardiovascular Imaging, 4(5):514-523 (Sep. 2011).
Sirois, et al., Hemodynamic Impact of Transcatheter Aortic Valve Deployment Configuration, Journal of Medical Devices, 7(4):040922.1-040922.2 (Dec. 2013).
Steinberg, Cardiac Conduction System Disease After Transcatheter Aortic Valve Replacement, American Heart Journal, 164(5):664-671 (Nov. 2012).
International Search Report & Written Opinion dated Apr. 18, 2023 in Int'l PCT Patent Appl. No. PCT/EP2023/053366 (091001).

\* cited by examiner

METHOD AND SYSTEM FOR PATIENT-SPECIFIC VIRTUAL PERCUTANEOUS STRUCTURAL HEART INTERVENTION

CROSS-REFERENCE TO RELATED APPLICATIONS

This application is a national phase application under 35 U.S.C. § 371 of PCT/EP2019/055907, filed Mar. 8, 2019, which claims priority to European Patent Application Serial No. 18163655.6, filed Mar. 23, 2018, the entire contents of each of which are incorporated herein by reference.

FIELD OF THE INVENTION

The present invention relates to the field of pre-operative planning of percutaneous, such as transcatheter, structural heart interventions, e.g. valve treatment, such as valve implantation and/or repair. More in particular, the invention relates to pre-operative prediction of the risk a patient developing abnormalities as a result of transcatheter valve treatment.

BACKGROUND TO THE INVENTION

The left ventricle of the heart pumps the blood to the aorta through the aortic valve. Aortic (valve) stenosis is a pathology occurring when the aortic valve does not open fully because the leaflets calcify, thicken and stiffen and, as a result, the blood flow going from the heart to the systemic circulation decreases. Aortic stenosis manifests itself in elderly people, with a prevalence going from 1.3% in over 65 and 4% in over 85 year old people. Currently it is the most common valvular heart disease in the Western world and its prevalence is increasing with the aging population.

The standard treatment for an aortic stenosis is the Surgical Aortic Valve Replacement (SAVR) aiming at reproducing the correct function of the native valve with an implanted valve. This invasive procedure requires total anesthesia, sternotomy (open-heart surgery) and cardiopulmonary bypass (the blood is pumped and oxygenated using an external machine), and is associated with about 6% in-hospital mortality for over 65 year old patients. Moreover, at least one-third of the patients with severe aortic stenosis are denied valve surgery as the risks associated with surgery are too high.

Trans-catheter aortic valve implantation (TAVI) or transcatheter aortic valve replacement (TAVR) is a minimally-invasive procedure for treating aortic stenosis: (1) the valve (e.g. a bioprosthetic valve made of porcine pericardium sutured on a metal stent) is crimped inside a catheter, (2) the catheter is inserted, for example, in the femoral artery, (3) pushed upstream along the aorta up to the aortic annulus and (4) the new valve is deployed within the diseased native valve. TAVI has the potential of treating high-risk patients and replacing the SAVR with a minimally-invasive intervention (no need for open-heart surgery or cardiopulmonary bypass) which can be performed in e.g. about 80 minutes. Main TAVI complications are vascular injury, stroke, cardiac injury (heart block, coronary obstruction, cardiac perforation), aortic regurgitation, cardiac conduction abnormalities and valve misplacement. Accurate pre operative planning is crucial to select the optimal device size and to anticipate potential difficulties.

Undersizing of a valve implant may lead to paravalvular aortic regurgitation, while oversizing may result in a rupture of the aortic annulus or in a suboptimal functional behavior of the implant. Currently available planning tools (Philips, Siemens, Pie Medical, Paeion) provide insights into the patient anatomy and can, for example, be used to determine the size of the aortic annulus, or to measure the distance between the valve plane and the coronary ostia. A problem with these tools is that they do not provide preoperative insights into the interaction between a certain implant device and the specific patient anatomy, and can thus not be used to predict complications such as regurgitation. Such insights are extremely valuable for interventional cardiologists.

Another problem is that is difficult to reconstruct native leaflets from e.g. CT images. In the currently deployed methods, an incomplete leaflet image is obtained, comprising gaps whereby the gaps represent a lack of data.

Document US 2011/0153286 A1 discloses a method and system for virtual percutaneous valve implantation. In one embodiment of the application a patient-specific anatomical model of a heart valve is estimated based on 3D cardiac medical image data. An implant model representing a valve implant is virtually deployed into the patient-specific anatomical model of the heart valve. A library of implant models, each modeling geometrical properties of a corresponding valve implant, can be maintained. The implant models maintained in the library can be virtually deployed into the patient specific anatomical model of the heart valve to select one of the implant models for use in a percutaneous valve implantation procedure.

In WO2013/171039 A1 the present inventors described an improved method for providing preoperative insights into the interaction of an implant device and specific patient anatomy, for better prediction of complications, such as regurgitation, for better prediction of the hemodynamic performance of an implant deployed in an aortic valve, and for better patient selection and stratification. Also WO2013/171039 A1 provides a web-based pre-operative planning service for TAVI using computer simulations that predict stent frame deformation and incomplete frame apposition, allowing to assess the risk on regurgitation and other complications such as coronary obstruction and conduction abnormalities prior to the intervention.

In WO2016/177647 A1 the present inventors described method for determining a measure of a risk of a patient developing cardiac conduction abnormalities and/or disorders, such as left bundle-branch block (LBBB), as a result of transcatheter structural heart intervention, such a transcatheter cardiac valve implantation/replacement or repair.

The methods described above can be computationally heavy. This can result in waiting times of several hours or even days, before a clinician can obtain the results of the determination. Therefore there is a need for faster processing.

SUMMARY OF THE INVENTION

According to an aspect is provided a computer implemented method for selecting, from a series of cardiac implants having different sizes, the cardiac implant having optimum size, and optionally predicting an optimum deployment position, for cardiac implantation in a patient. The method includes obtaining data representative of a patient-specific three-dimensional image of a cardiac region. Such data can include a three-dimensional medical image, e.g. obtained by computer tomography (CT) or magnetic resonance imaging (MRI). The method can include obtaining data representative of a series of implant models representing a series of cardiac implants having different sizes. Such data can include a three-dimensional model, such as a computer aided design (CAD) model or a finite element model. The method includes predicting an optimum size, and optionally an optimum position, of the cardiac implant best matching a predefined criterion when deployed in the cardiac region. Determining the optimum size, and optionally position, can take into account cardiac implant deployment and deformation of the cardiac region. The predefined criterion can be a lowest risk of complications during and/or after deployment of the actual implant in the actual cardiac region of the patient. The complications can e.g. be mechanical complications (such as stress, strain, mechanical pressure, contact area), electrical complications (such as electrical conduction problems), hydraulical complications (such as blood flow, leakage, regurgitation), risk of misplacement of the implant, or the like. The criterion can e.g. be associated with optimum interaction between the implant and the cardiac region. The interaction can be at least one of mechanical interaction, such as contact pressure, strain, contact area; leakage; regurgitation; cardiac conduction abnormalities; risk of implant misplacement; or the like.

It is also possible that the predefined criterion is a best overall match of the cardiac implant size for the given cardiac region. Especially when comparing large numbers of clinical data of previous cardiac implants in cardiac regions, for a given cardiac region a best average size, and optionally position, can be determined in view of all potential complications encountered in the clinical data.

The predicting can include querying a database including a plurality of records, each record including data representative of a three-dimensional image of a cardiac region and an associated size, and optionally position, of the cardiac implant of the series in the cardiac region, e.g. as a result of cardiac implant deployment and deformation of the cardiac region. The record can include data representative of (an implant model representing) a cardiac implant of a predetermined size. Thus, different records may apply to differently sized cardiac implants. The predicting can include determining parameter values for a parametric model representation of the patient-specific cardiac region. A second parametric model predicts the optimum size, and optionally optimum position, of a cardiac implant of the series in the cardiac region, e.g. as a result of cardiac implant deployment and deformation of the cardiac region associated therewith, on the basis of the parameter values. The predicting can include entering the data representative of the patient-specific three-dimensional image of the cardiac region into an artificial intelligence device, such as a machine learning device, deep learning device, neural network. The artificial intelligence device is arranged for outputting the prediction of the optimum size, and optionally optimum position, of a cardiac implant of the series As will be further elucidated below, this provides the advantage that actual calculating of the best size, and optionally best position, of the cardiac implant in the cardiac region may be omitted. This may be beneficial for processing time.

The method provides the advantage that the size of the cardiac implant best matching the predefined criterion when deployed in the cardiac region can be predicted. Optionally, when multiple types of implant are available, the method allows predicting the type of the cardiac implant best matching the predefined criterion when deployed in the cardiac region. Optionally, when multiple types of implant are available at least some of which have multiple sizes, the method allows predicting the size and type of the cardiac implant best matching the predefined criterion when deployed in the cardiac region. Optionally, the method allows predicting the implant position of the cardiac implant best matching the predefined criterion when deployed in the cardiac region.

According to an aspect the predicting can include querying a database including a plurality of records, each record including data representative of a three-dimensional image of a cardiac region and an associated size, and optionally position, of the cardiac implant in the cardiac region. The record can include data representative of the predefined criterion. The record can for instance include a three-dimensional medical image of a cardiac region. The record can include a model, such as a finite element model, representative of a cardiac region.

Optionally, the database includes records, each associated with a respective patient-specific clinical data. The database can include a plurality of three-dimensional medical images of cardiac regions of respective patients. The records can include data representative of implants implanted in the cardiac regions of the respective patients. The records can include data representative of the predetermined criterion. The database can include a plurality of models, such as finite element models, representative of cardiac regions of respective patients. Alternatively, or additionally, the database includes records associated with simulated data. The simulated data can be simulations of medical images of cardiac regions of respective patients. The simulated data can be models, such as a finite element models, representative of cardiac regions of respective patients.

Optionally, the database includes records obtained by applying augmentation techniques to other records, such as scaling, modifying a histogram, or the like. Thus, multiple records may be generated on the basis of a single dataset of clinical data or simulated data.

Optionally, the querying of the database includes determining the record associated with data representative of a three-dimensional image of a cardiac region closest matching the data representative of the patient-specific three-dimensional image of the cardiac region, e.g. using extreme gradient boosting. Optionally, the querying of the database includes determining the record associated with data representative of a three-dimensional image of a cardiac region closest matching the data representative of the patient-specific three-dimensional image of the cardiac region, and best matching the predetermined criterion. Querying the database can include comparing the patient-specific three-dimensional image of the cardiac region with three-dimensional images of a cardiac regions in the records in the database. A closest match between the patient-specific data and a particular record can be based on a quantified similarity, e.g. a similarity threshold. Once the record closest matching the data representative of the patient-specific three-dimensional image of the cardiac region has been determined, the size, and optionally position, associated with that record can be selected as prediction for the optimum size, and optionally optimum position, of the actual cardiac implant in the actual cardiac region of the patient best matching the predefined criterion.

According to an aspect the predicting can include determining parameter values for a parametric model representation of the patient-specific cardiac region. The second parametric model predicts the size, and optionally position of the cardiac implant in the cardiac region as a result of cardiac implant deployment and deformation of the cardiac region associated therewith on the basis of the parameter values. Once the parameter values have been determined according to which the parametric model of the cardiac region provides the closest match to the data representative of the patient-specific three-dimensional image of the cardiac region, these parameters, and optionally the predetermined criterion, can be used in the second parametric model for the size, and optionally position, for determining a prediction for the optimum size, and optionally optimum position, of the cardiac implant in the patient-specific cardiac region best matching the predefined criterion. The parametric model can e.g. model a three-dimensional image of the cardiac region, such as a three-dimensional medical image, or a model, such as a finite element model.

According to an aspect the predicting can include entering data representative of the patient-specific three-dimensional image of the cardiac region into an artificial intelligence device. Optionally, the predicting can include entering data representative of the predetermined criterion into the artificial intelligence device. The artificial intelligence device can use the data representative of the patient-specific three-dimensional image of the cardiac region, and optionally the predetermined criterion, as input, and return a prediction for the optimum size, and optionally optimum position, of the cardiac implant in the patient-specific cardiac region best matching the predefined criterion. The data representative of the patient-specific three-dimensional image of the cardiac region can e.g. include a three-dimensional image, such as a medical image, or a model, such as a finite element model.

Optionally, the method includes determining parameter values for a parametric model representation of the patient-specific cardiac region and querying a database including a plurality of records, each record including data representative of parameter values and an associated size, and optionally position of a cardiac implant. Hence, the size, and optionally position, can be predicted on the basis of a combination of a parametric model and querying a database. Querying the database can include comparing parameters associated with a cardiac anatomy of the patient with parameters associated with anatomies in the records in the database.

Optionally, the parameter values for the parametric model representation of the patient-specific cardiac region are determined by querying a database including a plurality of records, each record including data representative of a three-dimensional image of a cardiac region and associated parameter values. Alternatively, or additionally, the parameter values for the parametric model representation of the patient-specific cardiac region can be determined by entering the data representative of the patient-specific three-dimensional image of the cardiac region into an artificial intelligence device arranged for outputting the parameter values.

Optionally, the data representative of the series of implant models represents a series of cardiac implants having different types and sizes. The predicting can then include predicting the type and size, and optionally position, of the cardiac implant best matching the predefined criterion when deployed in the cardiac region as a result of cardiac implant deployment and deformation of the cardiac region. The different types can e.g. relate to different manufacturers, materials used, or the like.

Optionally, the predicting is further based on metadata with respect to the patient, such as demographic data, known pathology, medicament use, etc.

According to an aspect, in the a computer implemented method for selecting, from a series of cardiac implants having different sizes, the cardiac implant having optimum size, and optionally predicting an optimum deployment position, for cardiac implantation in a patient, the step of predicting an optimum size, and optionally an optimum position, of the cardiac implant best matching a predefined criterion when deployed in the cardiac region includes a) querying the database for identifying a record matching the patient-specific data better than a predetermined similarity threshold, and b) if no such record is found, calculating the optimum size, and optionally optimum position, of the cardiac implant in the patient-specific cardiac region. The calculating can include obtaining a patient-specific three-dimensional anatomical model representing the patient-specific cardiac region on the basis of the data representative of the patient-specific three-dimensional image of the cardiac region, said patient-specific anatomical model comprising a finite element mesh. The calculating can include obtaining a plurality of implant models, each representing a finite element representation of the cardiac implant of a predetermined size. The calculating can include virtually deploying said implant models into said patient-specific anatomical model. The calculating can include calculating an interaction between each of the deployed implant models and the patient-specific anatomical model, optionally at a plurality of deployment locations of the implant models. The calculating can include determining the optimum size, and optionally optimum position, on the basis of the calculated interactions.

A record can be generated including data representative of the three-dimensional image of the cardiac region and the associated size, and optionally position, of the implant. The record can be stored in the database.

According to an aspect is provided a computer implemented method for estimating a risk of complications arising in and/or after structural heart intervention. The method includes obtaining data representative of a patient-specific three-dimensional image of a cardiac region. The method includes obtaining data representative of a size, and optionally type, of cardiac implant to be implanted in the cardiac region of the patient. The method includes predicting an interaction between the cardiac implant and cardiac region, e.g. as a result of cardiac implant deployment and deformation of the cardiac region. The predicting includes querying a database including a plurality of records, each record including data representative of a three-dimensional image of a cardiac region, an associated size, and optionally type, of a cardiac implant, and an interaction; and/or determining parameter values for a parametric model representation of the patient-specific cardiac region and implant combination and using the parameter values in a third parametric model predicting the interaction; and/or entering the data representative of the patient-specific three-dimensional image of the cardiac region and size, and optionally type, of the cardiac implant into an artificial intelligence device arranged for outputting the prediction of the interaction. The prediction of the interaction can be a measure for the estimated risk.

The interaction can be at least one of mechanical interaction, such as contact pressure, strain, contact area; leakage; regurgitation; cardiac conduction abnormalities; implant misplacement; or the like.

Querying the database can include comparing the patient-specific three-dimensional image of the cardiac region with three-dimensional images of a cardiac regions in the records in the database. A closest match between the patient-specific data and a particular record can be based on a quantified similarity, e.g. a similarity threshold.

According to an aspect is provided a computer implemented method for planning structural heart intervention. The method includes obtaining data representative of a patient-specific three-dimensional image of a cardiac region. The method includes obtaining data representative of a cardiac implant, such as size and optionally type, to be implanted in the cardiac region of the patient. The method includes predicting a deployed shape of the cardiac implant in the cardiac region, e.g. as a result of cardiac implant deployment and deformation of the cardiac region. The predicting includes querying a database including a plurality of records, each record including data representative of a three-dimensional image of a cardiac region, a cardiac implant, and an a deployed shape of the cardiac implant; and/or determining parameter values for a parametric model representation of the patient-specific cardiac region and implant combination and using the parameter values in a third parametric model predicting the deployed shape of the cardiac implant; and/or entering the data representative of the patient-specific three-dimensional image of the cardiac region and the cardiac implant into an artificial intelligence device arranged for outputting the prediction of the deployed shape of the cardiac implant. The prediction of the deployed shape can be presented to a user, e.g. as an overlay on, e.g. a view of, the patient-specific three-dimensional image of the cardiac region.

Optionally, in the computer implemented method for planning structural heart intervention, the step of predicting the deployed shape of the cardiac implant in the cardiac region includes a) querying the database for identifying a record matching the patient-specific data better than a predetermined similarity threshold, and b) if no such record is found, calculating the deployed shape of the cardiac implant in the patient-specific cardiac region. The calculating can include obtaining a patient-specific three-dimensional anatomical model representing the patient-specific cardiac region on the basis of the data representative of the patient-specific three-dimensional image of the cardiac region, said patient-specific anatomical model comprising a finite element mesh. The calculating can include obtaining an implant models representing a finite element representation of the cardiac implant. The calculating can include virtually deploying said implant model into said patient-specific anatomical model. The calculating can include calculating a deployed shape of the cardiac implant, optionally at a plurality of deployment locations of the implant model.

Optionally, the method for planning structural heart intervention includes determining a neo-LVOT area, e.g. from the overlay.

A record can be generated including data representative of the three-dimensional image of the cardiac region and the associated deployed shape of the cardiac implant in the cardiac region. The record can be stored in the database.

According to an aspect is provided a computer implemented method for determining a neo-LVOT area. The method includes obtaining data representative of a patient-specific three-dimensional image of a cardiac region. The method includes obtaining data representative of a mitral valve implant, such as a size and optionally type, to be implanted in the mitral valve annulus region of the patient. The method includes predicting a deployed shape of the mitral valve implant in the mitral valve annulus region, e.g. as a result of mitral valve implant deployment and deformation of the mitral valve annulus region. The predicting includes querying a database including a plurality of records, each record including data representative of a three-dimensional image of a mitral valve annulus region, and an associated deployed shape of the mitral valve implant; and/or determining parameter values for a parametric model representation of the patient-specific mitral valve annulus region and mitral valve implant combination and using the parameter values in a third parametric model for predicting the deployed mitral valve implant shape; and/or entering the data representative of the patient-specific three-dimensional image of the mitral valve annulus region and of the mitral valve implant into an artificial intelligence device arranged for outputting the prediction of the deployed shape of the mitral valve implant. The prediction of the deployed shape can be presented to a user, e.g. as an overlay on, e.g. a view of, the patient-specific three-dimensional image of the mitral valve annulus region. The method can include determining the neo-LVOT area from the patient-specific three-dimensional image of the mitral valve annulus region and the predicted deployed shape of the mitral valve implant, e.g. from the overlay of the predicted deployed shape of the mitral valve implant on, e.g. a view of, the patient-specific three-dimensional image of the mitral valve annulus region. The neo-LVOT area can be determined by the computer. Alternatively, the neo-LVOT area can be determined, e.g. estimated, by a person, e.g. based on the overlay of the predicted deployed shape of the mitral valve implant on, e.g. a view of, the patient-specific three-dimensional image of the mitral valve annulus region.

Optionally, in the computer implemented method for determining a neo-LVOT area, the step of predicting the deployed shape of the mitral valve implant in the mitral valve annulus region includes a) querying the database for identifying a record matching the patient-specific data better than a predetermined similarity threshold, and b) if no such record is found, calculating the deployed shape of the mitral valve implant in the patient-specific mitral valve annulus region. The calculating can include obtaining a patient-specific three-dimensional anatomical model representing the patient-specific mitral valve annulus region on the basis of the data representative of the patient-specific three-dimensional image of the mitral valve annulus region, said patient-specific anatomical model comprising a finite element mesh. The calculating can include obtaining a mitral valve implant model, representing a finite element representation of the mitral valve implant. The calculating can include virtually deploying said mitral valve implant model into said patient-specific anatomical model. The calculating can include calculating an interaction between the deployed mitral valve implant models and the patient-specific anatomical model. The calculating can include determining the deployed shape, and optionally position, of the mitral valve implant on the basis of the calculated interaction.

A record can be generated including data representative of the three-dimensional image of the cardiac region and the associated deployed shape of the cardiac implant in the cardiac region. The record can be stored in the database.

According to an aspect the above methods can include a sub-method for generating a record for storage in a database. These records can be used for querying, for generating the parametric model(s), and/or for training the neural network. The sub-method can include obtaining a patient-specific three-dimensional anatomical model representing the patient-specific cardiac region on the basis of the data representative of the patient-specific three-dimensional image of the cardiac region, said patient-specific anatomical model comprising a finite element mesh. The sub-method can include obtaining an implant model representing a finite element representation of the cardiac implant of a predetermined size. The sub-method can include virtually deploying said implant model into said patient-specific anatomical model. The sub-method can include calculating an interaction between the deployed implant model and the patient-specific anatomical model. The sub-method can include generating a record including data representative of the three-dimensional image of the cardiac region and the associated size and interaction. The sub-method can include storing the record in the database. It will be appreciated that these calculations can be performed off-line and need not affect the speed at which the size, and optionally position, and/or interaction are determined from the data representative of the patient-specific three-dimensional image of the cardiac region according to the methods described above.

Optionally, for each obtained data representative of the patient-specific three-dimensional image of the cardiac region the sub-method is performed so as to be able to increase the size of the database, and hence the accuracy of the method.

According to an aspect the method can include an alternative or additional sub-method. This sub-method can include obtaining data representative of a post-operative patient-specific three-dimensional image of a cardiac region including a deployed cardiac implant. The sub-method can include determining a size and/or position of the deployed implant in the patient-specific cardiac region. The sub-method can include determining an interaction between the deployed implant and the patient-specific cardiac region. The sub-method can include generating a record including data representative of the post-operative three-dimensional image of the cardiac region and the associated size, and optionally position, and/or interaction of the cardiac implant of specific size in the cardiac region. The sub-method can include storing the record in a database. This sub-method provides the advantage that the generated records relate to actual real-world data, and hence can be used for making the method more accurate.

According to an aspect the method can include an alternative or additional sub-method. This sub-method can include using a neural network for generating a record including data representative of a three-dimensional image of a cardiac region and an associated size, and optionally position, and/or interaction of a cardiac implant of predetermined size in the cardiac region, and storing the record in a database.

According to an aspect is provided a method including using an artificial intelligence device for determining a finite element model of the patient-specific cardiac region, on the basis of the data representative of the patient-specific three-dimensional image of the cardiac region.

According to an aspect is provided a method including using an artificial intelligence device for determining the shape and/or position of the cardiac implant in the cardiac region as a result of cardiac implant deployment and deformation of the cardiac region, on the basis of a finite element model of the patient-specific cardiac region.

According to an aspect is provided a computer implemented method for patient-specific virtual percutaneous, such as transcatheter, structural heart intervention. The method includes obtaining data representative of a patient-specific three-dimensional image of a cardiac region. The method includes determining a patient-specific three-dimensional anatomical model comprising a finite element mesh representing the patient-specific cardiac region by: querying a database including a plurality of records, each record including data representative of a three-dimensional image of a cardiac region and data representative of an associated three-dimensional anatomical model; and/or determining parameter values for a parametric model representation of the patient-specific cardiac region; and/or entering data representative of the patient-specific three-dimensional image of the cardiac region into an artificial intelligence device, such as a neural network. The method includes obtaining an implant model representing a finite element representation of the cardiac implant. The method includes virtually deploying said implant model into said patient-specific anatomical model. The method includes calculating a shape and/or position of the deployed implant model as a result of implant model deployment and deformation of the patient-specific anatomical model.

The database can include a plurality of records, each record including data representative of a three-dimensional image of a cardiac region and data representative of an associated three-dimensional anatomical model. Determining the record associated with the data representative of a three-dimensional closest matching the patient-specific cardiac region provides the data representative of an estimate of the patient-specific anatomical model.

The parametric model models the patient-specific cardiac region. The determining can include determining parameter values for the parametric model representation of the patient-specific cardiac region. The parametric model can have a parametric model for the anatomical model. Once the parameter values have been determined according to which the parametric model of the cardiac region provides the closest match to the data representative of the patient-specific three-dimensional image of the cardiac region, these parameters can be used in the parametric model for the anatomical model for determining a prediction for the patient-specific anatomical model.

The artificial intelligence device can use the data representative of the patient-specific three-dimensional image of the cardiac region as input, and return a prediction for the patient-specific anatomical model.

According to an aspect is provided a system for selecting, from a series of cardiac implants having different sizes, the cardiac implant having optimum size, and optionally for predicting an optimum deployment position, for implantation in a patient. The system includes a processor. The processor is arranged for obtaining data representative of a patient-specific three-dimensional image of a cardiac region. The processor is arranged for obtaining data representative of a series of cardiac implants having different sizes. The processor is arranged for predicting the optimum size, and optionally position, of the cardiac implant best matching a predefined criterion when deployed in the cardiac region, e.g. as a result of cardiac implant deployment and deformation of the cardiac region. The predicting includes querying a database including a plurality of records, each record including data representative of a three-dimensional image of a cardiac region and an associated size, and optionally position, of a cardiac implant of the series; and/or determining parameter values for a parametric model representation of the patient-specific cardiac region and using the parameter values in a second parametric model predicting the optimum size, and optionally optimum position, of a cardiac implant of the series; and/or entering the data representative of the patient-specific three-dimensional image of the cardiac region into an artificial intelligence device arranged for outputting the prediction of the optimum size, and optionally optimum position, of a cardiac implant of the series.

According to an aspect is provided a system for estimating a risk of complications arising in or after structural heart intervention. The system includes a processor. The processor is arranged for obtaining data representative of a patient-specific three-dimensional image of a cardiac region. The processor is arranged for obtaining data representative of a size, and optionally type, of cardiac implant to be implanted in the cardiac region of the patient. The processor is arranged for predicting an interaction between the cardiac implant and cardiac region, e.g. as a result of cardiac implant deployment and deformation of the cardiac region. The predicting includes querying a database including a plurality of records, each record including data representative of a three-dimensional image of a cardiac region, an associated size, and optionally type, of a cardiac implant, and an interaction; and/or determining parameter values for a parametric model representation of the patient-specific cardiac region and implant combination and using the parameter values in a third parametric model predicting the interaction; and/or entering the data representative of the patient-specific three-dimensional image of the cardiac region and size, and optionally type, of the cardiac implant into an artificial intelligence device arranged for outputting the prediction of the interaction; wherein the prediction of the interaction is a measured for the estimated risk.

Optionally, the processor is included by a network server arranged for receiving the data representative of the patient-specific three-dimensional image of the cardiac region via the network from a user device, and for transmitting data representative of the determined size and/or interaction to the user device. The network can be the internet.

According to an aspect is provided a computer program product for selecting, from a series of cardiac implants having different sizes, the cardiac implant having optimum size, and optionally predicting an optimum deployment position, for implantation in a patient, including computer implementable instructions which when implemented by a programmable computer cause the computer to obtain data representative of a patient-specific three-dimensional image of a cardiac region; predict the optimum size, and optionally optimum position, of the cardiac implant best matching a predefined criterion when deployed in the cardiac region, e.g. as a result of cardiac implant deployment and deformation of the cardiac region; wherein the predicting includes querying a database including a plurality of records, each record including data representative of a three-dimensional image of a cardiac region and an associated size, and optionally position, of a cardiac implant of the series; and/or determining parameter values for a parametric model representation of the patient-specific cardiac region and using the parameter values in a second parametric model predicting the optimum size, and optionally optimum position, of a cardiac implant of the series; and/or entering the data representative of the patient-specific three-dimensional image of the cardiac region into an artificial intelligence device arranged for outputting the prediction of the optimum size, and optionally optimum position, of a cardiac implant of the series.

According to an aspect is provided a computer program product for estimating a risk of complications arising in or after structural heart intervention including computer implementable instructions which when implemented by a programmable computer cause the computer to obtain data representative of a patient-specific three-dimensional image of a cardiac region; obtain data representative of a size, and optionally type, of cardiac implant to be implanted in the cardiac region of the patient; predict an interaction between the cardiac implant and cardiac region, e.g. as a result of cardiac implant deployment and deformation of the cardiac region; wherein the predicting includes querying a database including a plurality of records, each record including data representative of a three-dimensional image of a cardiac region, an associated size, and optionally type, of a cardiac implant, and an interaction; and/or determining parameter values for a parametric model representation of the patient-specific cardiac region and implant combination and using the parameter values in a third parametric model predicting the interaction; and/or entering the data representative of the patient-specific three-dimensional image of the cardiac region and size, and optionally type, of the cardiac implant into an artificial intelligence device arranged for outputting the prediction of the interaction.

According to an aspect is provided a method for predicting a measure of a risk of a patient developing cardiac conduction abnormalities and/or disorders, such as left bundle-branch block (LBBB), as a result of transcatheter structural heart intervention, such a transcatheter cardiac valve treatment. The treatment may be trans-catheter valve implantation/replacement or trans-catheter valve repair. The transcatheter cardiac valve may e.g. be a transcatheter aortic or mitral valve. The method includes providing a patient-specific data set, such as an image, representing a patient-specific cardiac region, such as a patient-specific cardiac valve region. The patient-specific data set may represent a patient-specific aorta. The method includes predicting a measure of a mechanical interaction between the implant model and the patient-specific cardiac valve region. This prediction can be performed in similar ways as described above. The measure of the mechanical interaction represents a prediction of a mechanical interaction between the cardiac implant and the cardiac region of the patient. On the basis of the predicted mechanical interaction, a measure is determined of the risk of the patient developing cardiac conduction abnormalities and/or disorders.

Predicting the mechanical interaction between a cardiac valve implant and a cardiac valve region of the patient is an example of the present invention. The invention can also be applied to other implants, such as stents. Although below is referred in particular to a cardiac valve implant and a cardiac valve region of the patient, it will be appreciated that the features and advantages also apply to other implants for the heart. Therefore, for the purpose of understanding the invention where below is referred to a cardiac valve implant and cardiac valve region this similarly holds for other cardiac implants and/or other cardiac regions.

The measure of the mechanical interaction may include a measure of contact pressure between the cardiac valve implant and the cardiac valve region of the patient. The predicted contact pressure represents a prediction of a pressure between the cardiac valve implant and the cardiac valve region of the patient. On the basis of the predicted contact pressure, a measure can be determined of the risk of the patient developing cardiac conduction abnormalities and/or disorders. Alternatively, or additionally, the measure of the mechanical interaction may include a measure of strain in the tissue in the cardiac valve region of the patient due to the presence of the cardiac valve implant. The predicted strain represents a prediction of a strain in the tissue in the cardiac valve region of the patient. On the basis of the predicted strain, a measure can be determined of the risk of the patient developing cardiac conduction abnormalities and/or disorders.

It will be appreciated that this method provides the advantage that the measure of the risk of the patient developing cardiac conduction abnormalities and/or disorders, such as left bundle-branch block (LBBB), as a result of transcatheter treatment of the cardiac valve can be predicted pre-operatively. Hence, it is possible to predict how likely the TAVI or TAVR procedure will result in cardiac conduction problems. As a result, it may be predicted whether the TAVI or TAVR procedure ultimately may necessitate the implantation of a cardiac pacemaker. Alternatively, the method allows to predict the risk of conduction problems for a plurality of different transcatheter cardiac valves. This, in turn, may allow to select the optimum transcatheter cardiac valve for the specific patient.

Optionally, predicting the measure of the mechanical interaction includes predicting a measure of a surface area within which the predicted mechanical interaction exceeds a predetermined threshold. For example, predicting the measure of the contact pressure includes predicting a measure of a surface area within which the predicting pressure exceeds a predetermined threshold, i.e. a surface area within which the predicting pressure is not lower than the predetermined threshold. The risk of the patient developing cardiac conduction abnormalities and/or disorders can be quantified by predicting a surface area on the patient-specific anatomical model where the contact pressure exerted by the implant model onto the patient-specific anatomical model exceeds a predetermined threshold. A larger surface area can indicate a higher risk. It will be appreciated that an appropriate threshold level can be determined by calibration. Calibration may require determining the surface area in pre-operative anatomical models of a plurality of patients, and determining post-operatively whether or not these patients develop cardiac conduction abnormalities and/or problems. Alternatively, or additionally, predicting the measure of the strain can include predicting a measure of a surface area within which the predicted strain exceeds a predetermined threshold, i.e. a surface area within which the predicted strain is not lower than the predetermined threshold.

Optionally, predicting the measure of the contact pressure includes predicting a total contact force. The total contact force can be the predicted contact pressure integrated over the surface area of contact. A larger total force can indicate a higher risk.

Optionally, predicting the measure of the strain includes predicting a total strain. The total strain can be the predicted strain integrated over the surface area of contact. A larger total strain can indicate a higher risk.

Optionally, predicting the measure of the contact pressure includes predicting a peak pressure of the predicted pressure. A higher peak pressure can indicate a higher risk.

Optionally, predicting the measure of the strain includes predicting a peak strain of the predicted strain. A higher peak strain can indicate a higher risk.

Optionally, predicting the measure of the mechanical interaction includes predicting a location in the patient-specific anatomical model where the peak pressure or peak strain occurs. A location of the peak pressure or peak strain can indicate a measure of the risk. A combination of the location of the peak pressure and the value of the peak pressure can indicate a measure of the risk. A combination of the location of the peak strain and the value of the peak strain can indicate a measure of the risk.

Optionally, predicting the measure of the contact pressure includes defining a predetermined region of the patient-specific anatomical model, and predicting the measure of the contact pressure within that predetermined region. The predetermined region can e.g. be a region under the aortic annulus. The predetermined region can e.g. be a region on the left ventricular outflow tract under the aortic annulus. The predetermined region can e.g. be a region on the left ventricular outflow tract under the aortic annulus between the basal attachment points of the non- and right coronary leaflet. It will be appreciated that a region can be determined by calibration as described above, mutatis mutandis. Similarly, predicting the measure of the strain includes defining a predetermined region of the patient-specific anatomical model, and predicting the measure of the strain within that predetermined region.

Optionally, predicting the measure of the mechanical interaction includes defining a predetermined region of the patient-specific anatomical model, and predicting a measure of a surface area within the predetermined region within which the predicted pressure or strain exceeds a predetermined threshold.

Optionally, predicting the measure of the mechanical interaction includes defining a predetermined region of the patient-specific anatomical model, and predicting a total contact force or total strain within the predetermined region. The total contact force in the predetermined region can be the predicted contact pressure integrated over the surface area of the predetermined region. A larger total force or strain in the predetermined region can indicate a higher risk.

Optionally, predicting the measure of the mechanical interaction includes defining a predetermined region of the patient-specific anatomical model, and predicting a peak pressure or peak strain of the predicted pressure within the predetermined region. A higher peak pressure or strain can indicate a higher risk.

Optionally, predicting the measure of the mechanical interaction includes defining a predetermined region of the patient-specific anatomical model, and predicting a location in the patient-specific anatomical model where the peak pressure or peak strain within the predetermined region occurs. A location of the peak pressure or peak strain within the predetermined region can indicate a measure of the risk. A combination of the location of the peak pressure or strain and the value of the peak pressure or strain in the predetermined region can indicate a measure of the risk.

It will be appreciated that the risk of the patient developing cardiac conduction abnormalities and/or disorders can be quantified by taking a combination of the determinations mentioned above.

Optionally, the method includes estimating the patient-specific anatomical model on the basis of a, preferably preoperative, cardiovascular 2D or 3D medical image data, such as a CT-scan, an MRI image, echocardiography images or the like.

Optionally, the method includes estimating the patient-specific anatomical model on the basis of anatomical measurements, using for example, a parametric heart model.

Optionally, the method includes reporting the measure of the mechanical interaction to a user. The measure of mechanical interaction may e.g. be displayed on a display, printed in hardcopy or the like. It is also possible to report an indication of the risk of the patient developing cardiac conduction abnormalities to the user.

According to an aspect is provided a method for predicting a measure of hemodynamic compromise as a result of transcatheter structural heart intervention, such a transcatheter cardiac valve treatment. The treatment may be transcatheter valve implantation/replacement or trans-catheter valve repair. The transcatheter cardiac valve may e.g. be a transcatheter aortic or mitral valve or tricuspid valve. The method includes providing a patient-specific data set, such as an image, representing a patient-specific cardiac region including a deployment site for the cardiac implant in a first blood flow path, such as a patient-specific cardiac valve region, and a second blood flow path, such as a LVOT or aorta. The representation of the patient-specific cardiac region may represent a patient-specific left ventricle and/or atrium and/or aorta or a part thereof. The method includes, e.g. via predicting the shape and/or position of the cardiac implant in the cardiac region, predicting a measure of hemodynamic compromise in the deformed representation of the patient-specific cardiac region. This prediction can be performed in similar ways as described above. On the basis of the predicted measure of hemodynamic compromise, a measure may be determined of the risk of the patient developing complications if an actual implant corresponding to the implant model were actually implanted in the anatomical region of the patient corresponding to the patient-specific data set.

Alternatively, the method can include predicting an optimum implant size, and optionally type and/or position. The implant can e.g. be a transcatheter mitral valve, TMV, or transcatheter aortic valve, TAV, or transcatheter tricuspid valve.

The method can be used for predicting obstruction of the second blood flow path. Then, from the virtually deployed implant model and the deformed representation of the patient-specific cardiac region, a measure of obstruction of the second blood flow path in the deformed representation of the patient-specific cardiac region is predicted. On the basis of the predicted measure of obstruction, a measure may be determined of the risk of the patient developing complications if an actual implant corresponding to the implant model were actually implanted in the anatomical region of the patient corresponding to the representation of the patient-specific cardiac region.

The method can be used for predicting obstruction of the first blood flow path. For example, it is possible that with the valve leaflets open an open area of the valve is reduced, e.g. due to a not well expanded or deployed valve. This can cause a pressure drop (or gradient) in the blood flow through the valve. Then, from the virtually deployed implant model and the deformed representation of the patient-specific cardiac region, a measure of obstruction of the first blood flow path in the deformed patient-specific cardiac region is predicted. On the basis of the predicted measure of obstruction, a measure may be determined of the risk of the patient developing complications if an actual implant corresponding to the implant model were actually implanted in the anatomical region of the patient corresponding to the representation of the patient-specific cardiac region.

The method can be used for predicting leakage in the first blood flow path. For example, it is possible that with the valve leaflets closed blood leaks around the outside of the implanted valve, between the valve and the surrounding tissue. Alternatively, or additionally, in the closed position the valve leaflets may not fully close, allowing blood to leak through the implanted valve. Then, from the virtually deployed implant model and the deformed representation of the patient-specific cardiac region, a measure of leakage in the first blood flow path in the deformed patient-specific cardiac region is predicted. On the basis of the predicted measure of leakage, a measure may be determined of the risk of the patient developing complications if an actual implant corresponding to the implant model were actually implanted in the anatomical region of the patient corresponding to the representation of the patient-specific cardiac region.

A cardiac valve implant and a cardiac valve region of the patient is an example of the present invention. The invention can also be applied to other implants, such as stents. Although below is referred in particular to a cardiac valve implant and a cardiac valve region of the patient, it will be appreciated that the features and advantages also apply to other implants for the heart. Therefore, for the purpose of understanding the invention where herein is referred to a cardiac valve implant and cardiac valve region this similarly holds for other cardiac implants and/or other cardiac regions, including LAA, atrial or ventricular septal defect closure.

Optionally, the method includes providing the representation of the patient-specific cardiac region at a plurality of moments during the cardiac cycle, and predicting the measure of hemodynamic compromise, at the plurality of moments. It will be appreciated that the geometry of the heart changes significantly during the cardiac cycle. Therefore, the measure of hemodynamic compromise may vary significantly during the cardiac cycle as well. Hence, predicting the measure of hemodynamic compromise at a plurality of moments during the cardiac cycle allows to determine minimum and maximum values of the hemodynamic compromise.

Optionally, the measure of obstruction of the second blood flow path is a cross sectional area of the second blood flow path. The cross sectional area, for instance, e.g. substantially, orthogonal to the direction of blood flow has proven to be a reliable measure of obstruction. The cross sectional area of the second blood flow path after deployment of the implant model can be compared with a cross sectional area of the second blood flow path in the representation of the patient-specific cardiac region in which no implant model is deployed. This provides insight into the predicted change of cross sectional area available for blood flow after deployment of the implant. Also a volume reduction of a segment of the second blood flow path can be a good measure to quantify obstruction.

Optionally, the measure of obstruction of the second blood flow path is a ratio of a cross sectional area of the second blood flow path when the implant model is deployed divided by a cross sectional area of the second blood flow path in the representation of the patient-specific cardiac region in which no implant model is deployed. This takes into account deformation of the anatomy, e.g. a TMVR device pushing against the LVOT reducing LVOT area, and presence of the device, e.g. the remaining area is the deformed area minus area occupied by the device. The ratio provides insight into the predicted change of the cross sectional area due to implant deployment.

Optionally, the measure of obstruction of the first blood flow path is a cross sectional area of the first blood flow path, e.g. in view of valve leaflet positions. The cross sectional area, for instance, e.g. substantially, orthogonal to the direction of blood flow has proven to be a reliable measure of obstruction. The cross sectional area of the first blood flow path after deployment of the implant model can be compared with a cross sectional area of the first blood flow path in the representation of the patient-specific cardiac region in which no implant model is deployed. This provides insight into the predicted change of cross sectional area available for blood flow after deployment of the implant. Also a volume reduction of a segment of the first blood flow path can be a good measure to quantify obstruction.

Optionally, the measure of obstruction of the first blood flow path is a ratio of a cross sectional area of the first blood flow path when the implant model is deployed divided by a cross sectional area of the first blood flow path in the representation of the patient-specific cardiac region in which no implant model is deployed. The ratio provides insight into the predicted change of the cross sectional area due to implant deployment.

Optionally, the representation of the patient-specific cardiac region further includes fluid pressures in the cardiac region. Hence, deformation of the representation of the patient-specific cardiac region can be calculated taking into account the fluid pressure. It is also possible to use computational fluid dynamics, CFD. Hence, obstruction and/or leakage can be determined.

Optionally, the method includes the step of simulating a displacement of at least one valve leaflet of the cardiac valve implant. The measure of hemodynamic compromise, e.g. the measure of obstruction of the second blood flow path, can then be predicted also on the basis of the leaflet displacement.

Optionally, the method includes the step of simulating a displacement of at least one valve native leaflet due to device-anatomy interaction and optionally hydrodynamic forces. The measure of hemodynamic compromise, e.g. the measure of obstruction of the second blood flow path, can then be predicted also on the basis of the leaflet displacement.

Optionally, the displacement of the valve leaflet (of the implant and/or native valve) can be calculated using CFD, or fluid structure interactions, FSI. For example, the anterior mitral valve leaflet is displaced towards the LVOT by TMVR, but may further move during systole due to blood flow. This may be modelled as suggested.

Optionally, the measure of obstruction of the second blood flow path is a pressure gradient at the second blood flow path. Optionally, the measure of obstruction of the first blood flow path is a pressure gradient at the first blood flow path. Optionally, the measure of obstruction of the first blood flow path is a pressure gradient across the implant, e.g. the valve (i.e. non-zero pressure difference across the valve when valve is open).

Optionally, the measure of obstruction of the second blood flow path is a flow measure at the second blood flow path. Optionally, the flow measure is the maximum velocity at the second blood flow path or the extension of the cross sectional portion of the second blood flow path with velocity magnitude above a threshold. Optionally, the measure of obstruction of the first blood flow path is a flow measure at the first blood flow path. Optionally, the flow measure is the maximum velocity at the first blood flow path or the extension of the cross sectional portion of the first blood flow path with velocity magnitude above a threshold.

It will be appreciated that this method provides the advantage that the measure of the risk of the patient developing hemodynamic compromise, such as obstruction and/or leakage, as a result of transcatheter treatment of the cardiac valve can be predicted pre-operatively. Hence, it is possible to predict how likely e.g. a planned TAVI or TMVR procedure will result in hemodynamic problems.

Optionally, predicting the measure of hemodynamic compromise includes predicting an evolution of the hemodynamic compromise over time during the process of deployment. It is possible to predict the measure of hemodynamic compromise at a first moment and at a second moment. The first moment may be prior to the implant model being fully deployed into the patient-specific anatomical model. The second moment may be after the implant model has been fully deployed into the representation of the patient-specific cardiac region. It is also possible to predict the measure of the hemodynamic compromise at a plurality of first moments. Hence a time evolution of the hemodynamic compromise during deployment of the implant model can be predicted. Optionally, time evolution of hemodynamic compromise after deployment is also predicted. Hence, remodeling of the heart, due to the heart anatomy changing due to the prolonged presence of the implant, can be taken into account. For instance, hemodynamic compromise at one week, at one month, and at one year after treatment can be predicted.

Optionally, predicting the measure of hemodynamic compromise may include predicting a series of situations of progressing deployment of the implant model into the representation of the patient-specific cardiac region. The situations may progressively differ by a predetermined amount or ratio of deployment. The deployment can include insertion of the implant model into the representation of the patient-specific cardiac region. The insertion can include travel of a model of a, collapsed, implant along a vessel. The series of situations can include situations of progressively differing positions of insertion up to an intended deployment position. The deployment can include expansion of the implant model in the representation of the patient-specific cardiac region. The series of situations can include situations of progressively differing stages of expansion of the implant model. For each of the situations of the series of situations the measure of hemodynamic compromise can be predicted as described above. Hence, all stages of deployment can be modeled. The processing unit can be arranged to determine the situation of the series of situations in which the predicted hemodynamic compromise is most significant, e.g. highest obstruction. The processing unit may be arranged to determine the measure of hemodynamic compromise in the situation of the series of situations in which the predicted mechanical interaction is most significant, e.g. for predicting hemodynamic problems, e.g. highest. The series of situations may be generated for a plurality of different deployment sites. The processing unit may be arranged to select the optimum deployment site.

It will be appreciated that the risk of the patient developing hemodynamic problems can be quantified by taking a combination of the determinations mentioned above.

Optionally, the method includes estimating the patient-specific anatomical model on the basis of a, preferably preoperative, cardiovascular 2D or 3D or 4D medical image data, such as a X-rays, CT-scan, an MRI image, echocardiography images or the like, and combinations thereof.

Optionally, the method includes estimating the patient-specific anatomical model on the basis of anatomical measurements, using for example, a parametric heart model.

Optionally, the implant model comprises a finite element mesh. Each element of said mesh can be featured by a set of nodes. Adjacent elements of said element can comprise mutually shared nodes with said element. Said element can be featured by material dependent parameters. Each element of said mesh can differ in material dependent parameters from an adjacent element of said element of said mesh.

Optionally, the representation of the cardiac region is a finite element anatomical model. Optionally, stiffness elements are provided to a plurality of nodes of a mesh of the anatomical model. A stiffness element induces a reacting force on the corresponding node of said mesh, wherein said force is dependent on the displacement of said node or on the distance between said node and a fixed position equal or very close to the initial position of said node.

Optionally, the method includes predictions of deployment of the implant model into the representation of the patient-specific cardiac region at a plurality of different locations at and/or near the deployment site. Thus shape, position, measure of mechanical interaction, and/or measure of obstruction can be predicted for each of the different locations. Hence, it is possible to assess the risks for the plurality of different locations of the implant. Hence, it is also possible to select the location for the implant associated with the lowest risk of developing problems. Such selected location can be used in pre-operative planning of a TAVI or TMVR procedure.

Optionally, the method includes providing predictions for a plurality of implant models, each modeling geometrical and/or material properties of a corresponding implant; and virtually deployment of each of the implant models into the representation of the patient specific cardiac region. Thus shape, position, measure of mechanical interaction, and/or measure of obstruction can be predicted for each of the implant models. Hence, it is possible to assess the risks for each the plurality of different implant models. Hence, it is also possible to select the implant model associated with the lowest risk of developing problems. Such selected implant model can be used in pre-operative planning of a TAVI or TMVR or TTVR procedure. The method can include selecting a cardiac valve implant corresponding to one of the plurality of the implant models for a percutaneous implantation procedure. A cardiac valve implant associated with the selected implant model can be used in a percutaneous implantation procedure to minimize risk of the patient developing problems. It will be appreciated that it is also possible to predict virtual deployment of each implant model of the plurality of implant models into the patient specific anatomical model at a plurality of different locations at and/or near the deployment site. Thus the implant models can be compared each at its optimal location.

Optionally, the method includes reporting the results to a user. The results, e.g. the shape, position, measure of mechanical interaction, and/or measure of obstruction, may e.g. be displayed on a display, printed in hardcopy or the like. It is also possible to report an indication of the risk of the patient developing problems to the user.

It will be appreciated that all aspects, features and options mentioned in view of the methods apply equally to the systems and the computer program products, and vice versa.

BRIEF DESCRIPTION OF THE DRAWINGS

Embodiments of the present invention will now be described in detail with reference to the accompanying drawings in which.

DETAILED DESCRIPTION

Figure 1:
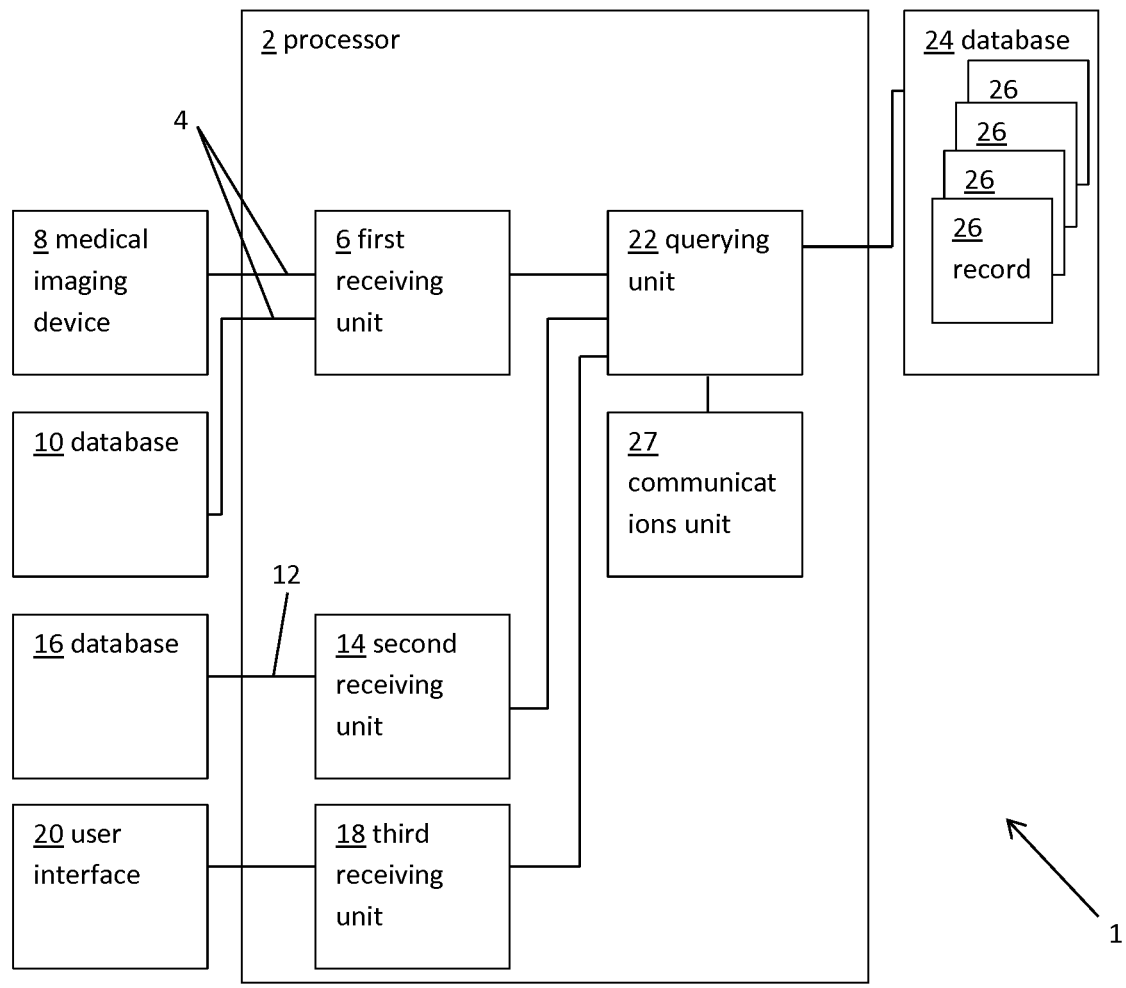
FIG. 1 shows an example of a system.

FIG. 1 shows an example of a system 1 for selecting a cardiac implant. The system is arranged for selecting, from a series of cardiac implants having different sizes, the cardiac implant having optimum size. Additionally, the system may be arranged for predicting an optimum deployment position of the selected cardiac implant for implantation in a patient.

The system includes a processor 2. The processor 2 is arranged for obtaining data 4 representative of a patient-specific three-dimensional, 3D, image of a cardiac region. Thereto the processor 2 can include a first receiving unit 6. In this example, the data 4 representative of a patient-specific three-dimensional image of a cardiac region includes a 3D medical image, e.g. obtained by computer tomography, CT, or magnetic resonance imaging, MRI. The data 4 representative of a patient-specific three-dimensional image of a cardiac region can be a 3D CT image and/or a 3D MRI image of the cardiac region of the patient under study. The first receiving unit 6 can be arranged for obtaining the data 4 from a medical imaging device 8 and/or from a database 10. The data 4 can e.g. be obtained from the imaging device 8 and/or the database 10 via a communications network such as the internet.

The processor 2 is arranged for obtaining data 12 representative of a series of cardiac implants having different sizes. The series of cardiac implants can e.g. include a series of cardiac implants of a first type, e.g. from one manufacturer, provided in a plurality of different sizes. The series of cardiac implants can include cardiac implants of multiple different types, e.g. from multiple manufacturers, having different sizes. The series of cardiac implants can include a first series of cardiac implants of a first type, having different sizes, and a cardiac implant (or a series of cardiac implants) of a second type. The processor 2 here includes a second receiving unit 14 for obtaining the data 12 representative of a series of cardiac implants having different sizes, e.g. from a database 16. The data 12 representative of a series of cardiac implants having different sizes can include an indication of the type of implant and an indication of a size of the implant. It will be appreciated that the implants can differ in a lateral dimension, such as a diameter. It is also possible that the implants differ in a longitudinal dimension, such as a length.

The processor 2 is arranged for predicting the optimum size of the cardiac implant best matching a predefined criterion when deployed in the cardiac region. Optionally the processor 2 is also arranged for predicting the optimum position of the selected cardiac implant in the cardiac region.

The predefined criterion can be a lowest risk of complications during and/or after deployment of the actual implant in the actual cardiac region of the patient. The complications can e.g. be mechanical complications (such as stress, strain, mechanical pressure, contact area), electrical complications (such as electrical conduction problems), hydraulical complications (such as blood flow, leakage, regurgitation), risk of misplacement of the implant, or the like. The criterion can e.g. be associated with optimum interaction between the implant and the cardiac region. The interaction can be at least one of mechanical interaction, such as contact pressure, strain, contact area; leakage; regurgitation; cardiac conduction abnormalities; risk of implant misplacement; or the like. It is also possible that the predefined criterion is a best overall match of the cardiac implant size for the given cardiac region. Especially when comparing large numbers of clinical data of previous cardiac implants in cardiac regions, for a given cardiac region a best average size, and optionally position, can be determined in view of all potential complications encountered in the clinical data.

In this example, the processing unit includes a third receiving unit 18. The third receiving unit 18 is arranged for receiving a user selection of the predefined criterion to be applied. The third receiving unit 18 can be coupled to a user interface 20. The user interface can selectably present a plurality of criterions to the user, allowing the user to select the criterion to be applied. It is also possible that the processor 2 is arranged for selecting a default predefined criterion in the absence of a user selection. It is also possible that the third receiving unit 18 is omitted, and the processor is arranged for using a predetermined predefined criterion, and/or for selecting a criterion, e.g. based on a rule.

In the example of FIG. 1, the processor 2 is arranged for predicting the optimum size of the cardiac implant best matching the predefined criterion when deployed in the cardiac region. Thereto the processing unit 2 includes a querying unit 22 arranged for querying a database 24. The database 24 includes a plurality of records 26. Each record 26 includes data representative of a three-dimensional image of a cardiac region and an associated size, and optionally position, of a cardiac implant of the series. Each record 26 can also include data representative of compliance to one or more of the criterions. The querying unit 22 is arranged for querying the database 24 for determining the record 26 including data representative of a three-dimensional image of a cardiac region that closest matches the data 4 representative of a patient-specific three-dimensional image of a cardiac region as obtained by the first receiving unit, e.g. using extreme gradient boosting. Herein, the querying unit can take the predefined criterion into account (e.g. best overall match if no specific criterion is selected). Once this closest matching record has been found, the querying unit 22 extracts from this record the data representative of the size, and optionally position, of the cardiac implant. The processor 2 uses this size as the prediction for the optimum size of the cardiac implant best matching the predefined criterion when deployed in the cardiac region. The prediction can be made knowable to the user, e.g. via the user interface, and/or via a communications unit 27, such as a messaging unit, e.g. an email unit.

The database 24 can include records 26 associated with respective patient-specific clinical data, and/or records associated with simulated data. The database 24 can include records obtained by applying augmentation techniques to other records, such as scaling, modifying a histogram, etc.

Figure 2:
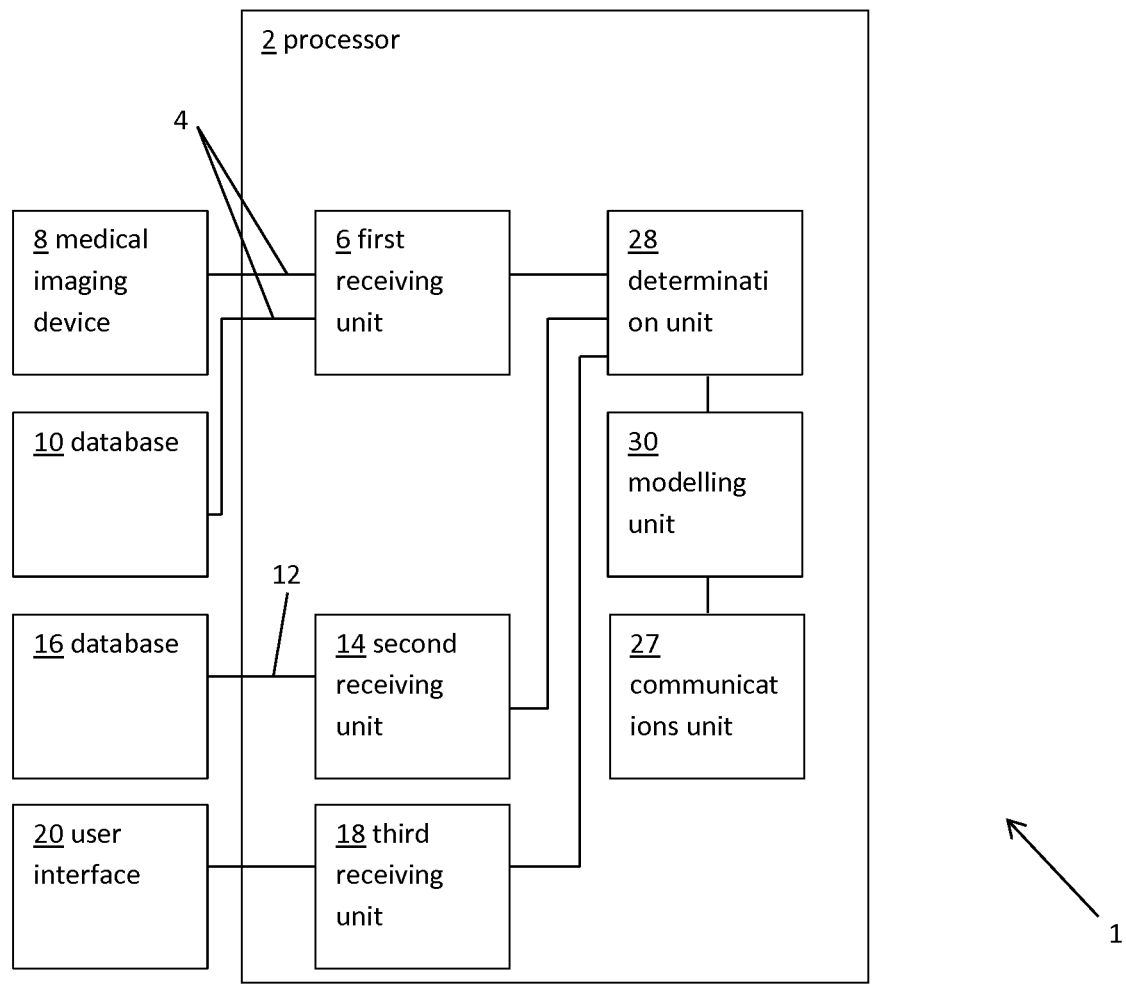
FIG. 2 shows an example of a system.

FIG. 2 shows another example of a system 1 for selecting a cardiac implant. The system of FIG. 2 is highly similar to the system as described in view of FIG. 1.

In the example of FIG. 2, the processor 2 is arranged for predicting the optimum size of the cardiac implant best matching the predefined criterion when deployed in the cardiac region. Thereto the processing unit 2 includes a determination unit 28 arranged for determining, on the basis of the data 4 representative of a patient-specific three-dimensional image of a cardiac region, parameter values for a first parametric model, providing a model representation of the patient-specific cardiac region. Hence, the determination unit 28 summarizes the patient-specific three-dimensional image of a cardiac region as one or more parameter values of the first parametric model. It will be appreciated that the predefined criterion can also be a parameter of the first parametric model. If no specific criterion is selected the criterion may not be a parameter of the first parametric model, and a default criterion can be used, e.g. best overall match.

The processor 2 includes a modelling unit 30. The modelling unit 30 includes a second parametric model. The second parametric model takes the parameter values of the first parametric model to predict the optimum size, and optionally optimum position, of the cardiac implant.

Figure 3:
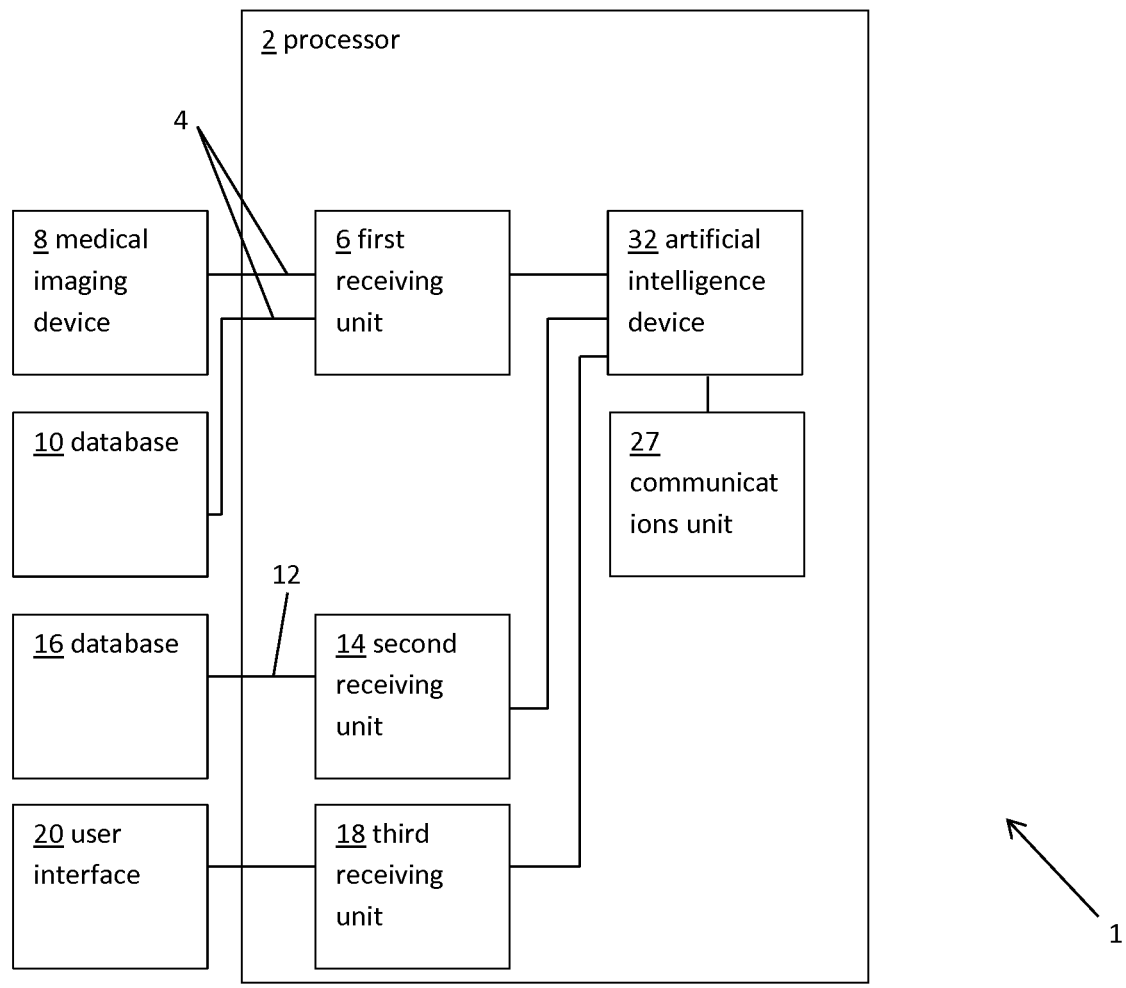
FIG. 3 shows an example of a system.

FIG. 3 shows another example of a system 1 for selecting a cardiac implant. The system of FIG. 3 is highly similar to the system as described in view of FIGS. 1 and 2.

In the example of FIG. 3, the processor 2 is arranged for predicting the optimum size of the cardiac implant best matching the predefined criterion when deployed in the cardiac region. Thereto the processing unit 2 includes an artificial intelligence device 32. The processing unit 2 is arranged for entering the data representative of the patient-specific three-dimensional image of the cardiac region into the artificial intelligence device 32. For example, a 3D CT image and/or a 3D MRI image of the cardiac region of the patient under study is entered into the artificial intelligence device 32. The artificial intelligence device 32 is arranged for outputting the prediction of the optimum size, and optionally optimum position, of the cardiac implant of the series. It will be appreciated that the predefined criterion can also be inputted to the artificial intelligence device. If no specific criterion is selected the criterion may not be inputter into the artificial intelligence device, and a default criterion can be used, e.g. best overall match.

It will be appreciated that the systems as described in relation to FIGS. 1, 2 and 3 can be combined. For example, in the system of FIG. 2, the parameter values for the first parametric model can e.g. be determined by querying a database including a plurality of records, each record including data representative of a three-dimensional image of a cardiac region and associated parameter values. It is also possible that the parameter values for the first parametric model are determined by entering the data representative of the patient-specific three-dimensional image of the cardiac region into an artificial intelligence device arranged for outputting the parameter values.

It will also be appreciated that the systems can apply a stepped approach. For instance, the querying unit 22 can in a first step query the database 24 for determining a set of records 26 including data representative of a three-dimensional image of a cardiac region that closest matches the data 4, and in a second step query the set of records for determining the record closest matching the predefined criterion.

The predicting can further be based on metadata with respect to the patient, such as demographic data, known pathology, medicament use, etc.

Figure 7:
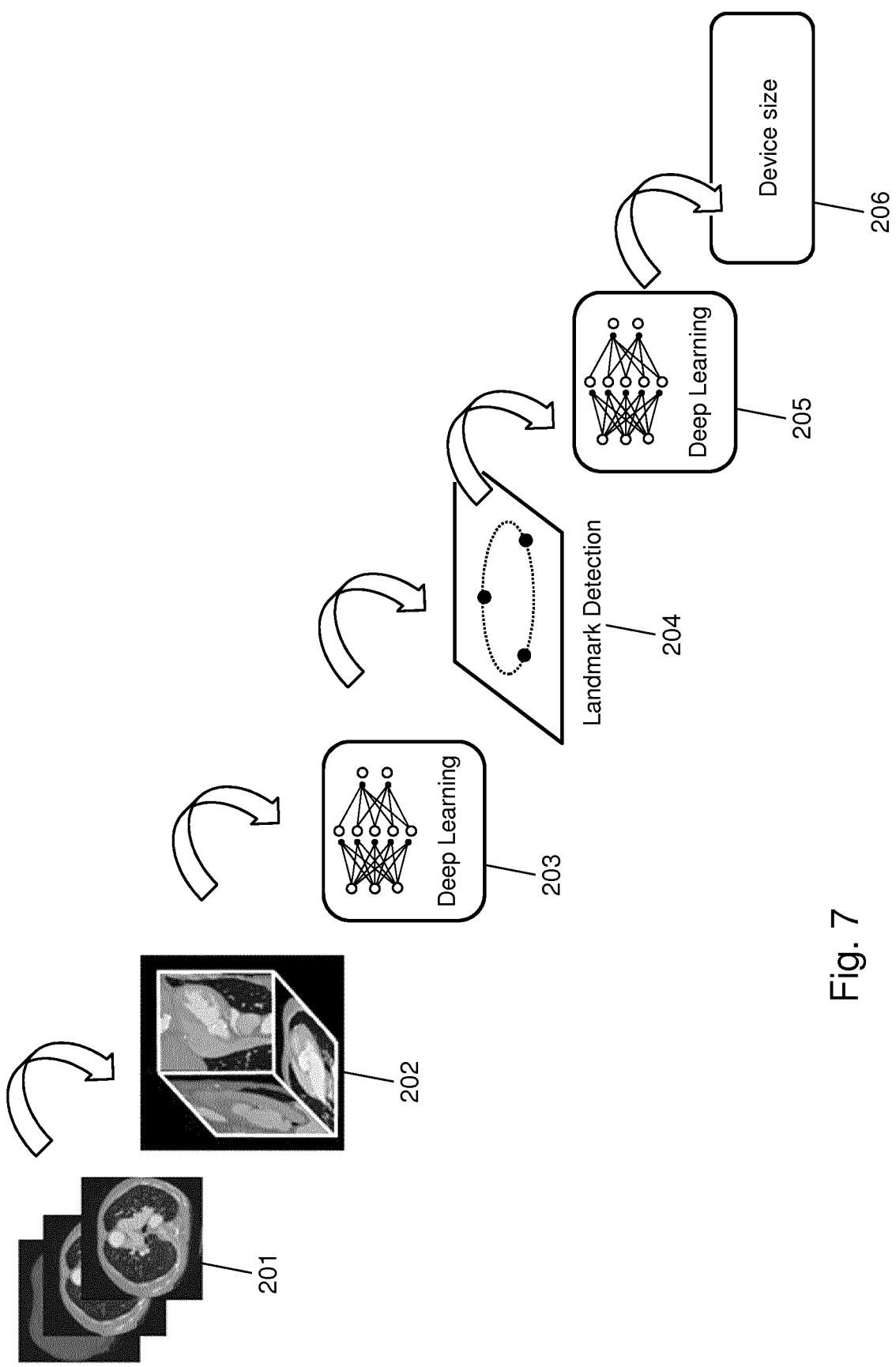
FIG. 7 shows an example of a method.

The system 1 as described with respect to FIG. 3 can e.g. be used as follows as elucidated in FIG. 7.

In step 201 data 4 representative of a patient-specific three-dimensional image of a cardiac region, here a plurality of CT images, is provided. In step 202 the data 4 representative of a patient-specific three-dimensional image of a cardiac region, in converted into a 3D CT image. In step 203 the data 4 is entered into the artificial intelligence device, here a deep learning device. In step 204 the artificial intelligence device determines in the 3D CT image a plurality of landmarks. In step 205 data representative of the landmarks is entered into the artificial intelligence device. In step 206 the artificial intelligence device outputs the prediction of the optimum size of the cardiac implant to be implanted in the cardiac region according to the CT images.

It will be appreciated that the systems of FIGS. 1, 2 and 3 can be used in preoperative planning. Using such system it can be determined which size implant of the plurality of sizes implants has the best chance of success, e.g. best fit and/or lowest risk of the patient developing complications. A cardiac implant corresponding to the predicted implant can then be selected for a real-life percutaneous implantation procedure.

Figure 4:
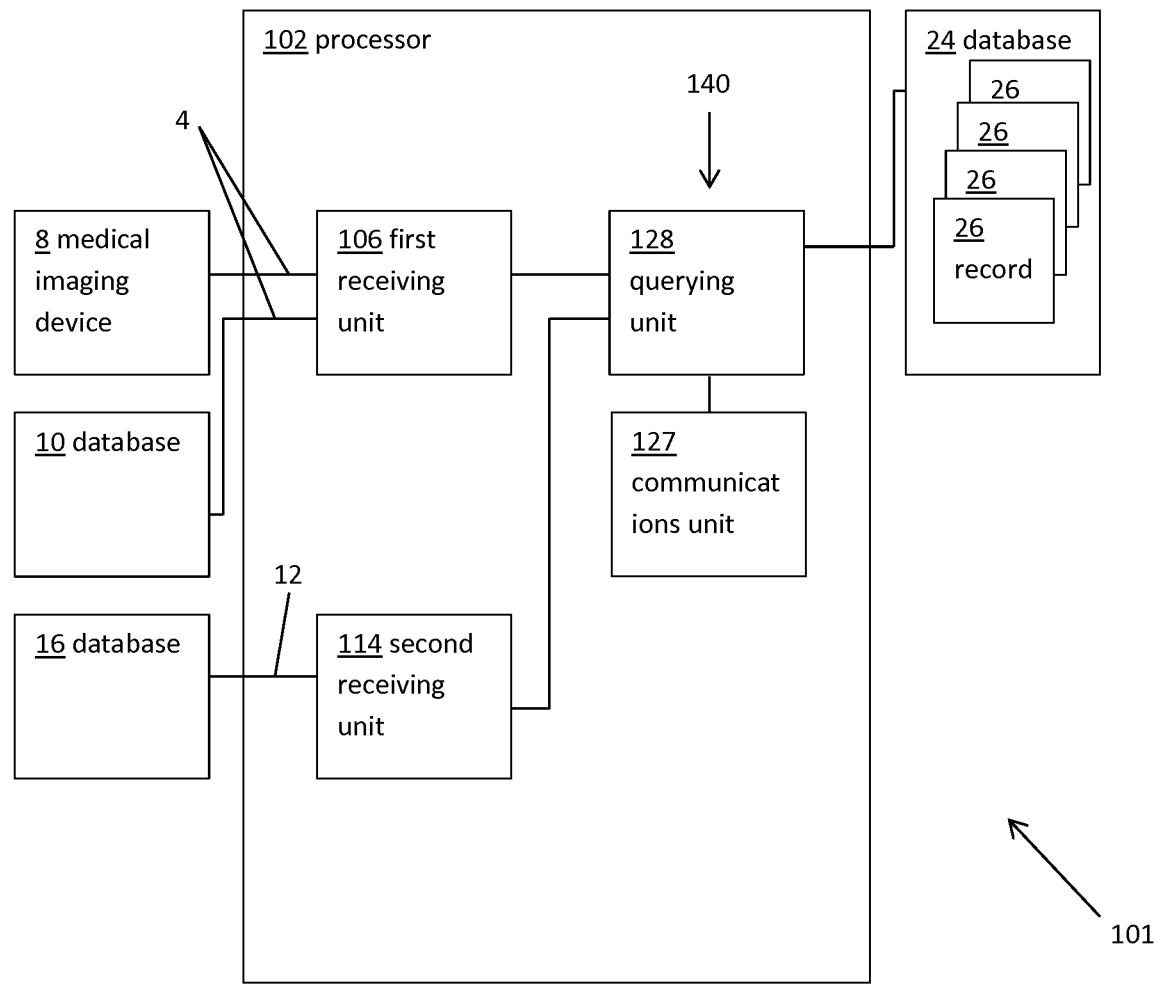
FIG. 4 shows an example of a system.
Figure 5:
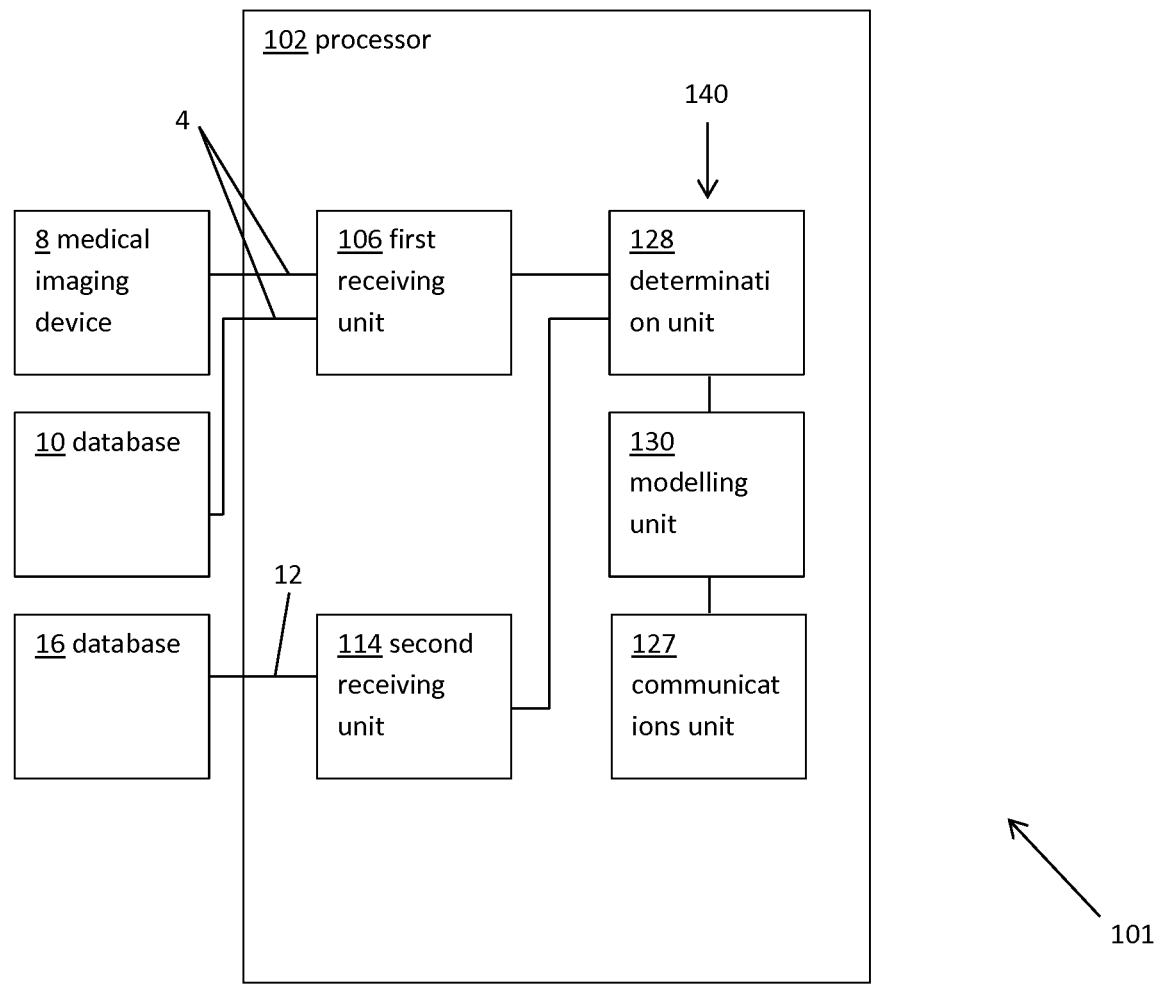
FIG. 5 shows an example of a system.
Figure 6:
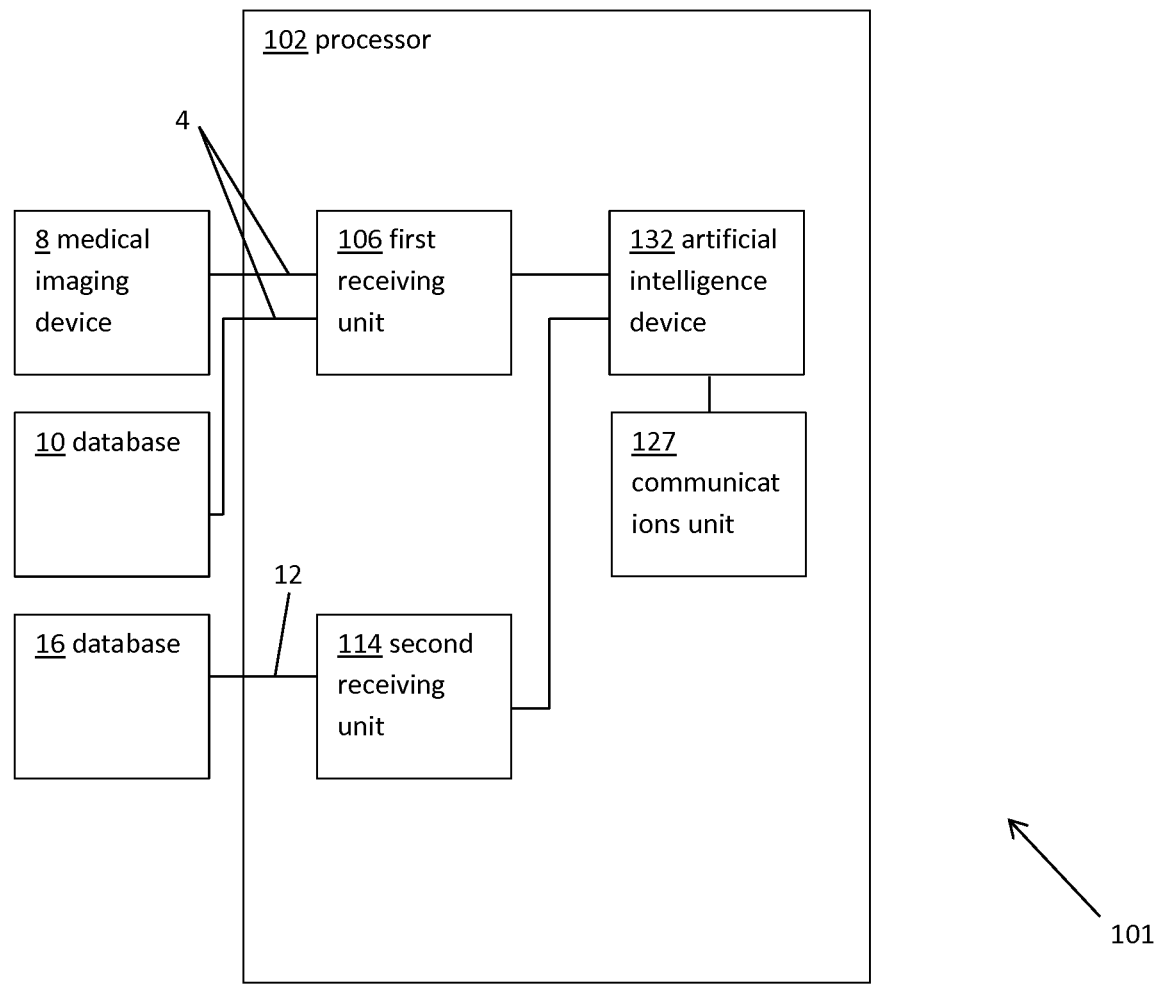
FIG. 6 shows an example of a system.

FIGS. 4, 5 and 6 show an examples of a system 101 for estimating a risk of complications arising in or after structural heart intervention. The system 101 including a processor 102. The processor includes a first receiving unit 106 arranged for obtaining data 4 representative of a patient-specific three-dimensional image of a cardiac region. In this example, the data 4 representative of a patient-specific three-dimensional image of a cardiac region includes a 3D medical image, e.g. obtained by computer tomography, CT, or magnetic resonance imaging, MRI. The data 4 representative of a patient-specific three-dimensional image of a cardiac region can be a 3D CT image and/or a 3D MRI image of the cardiac region of the patient under study. The first receiving unit 106 can be arranged for obtaining the data 4 from a medical imaging device 8 and/or from a database 10. The data 4 can e.g. be obtained from the imaging device 8 and/or the database 10 via a communications network such as the internet.

The system 101 includes a second receiving unit 114 arranged for obtaining data representative of a size, and optionally type, of cardiac implant to be implanted in the cardiac region of the patient, e.g. from a database 16.

The system 101 includes a predicting unit 140. The predicting unit 140 is arranged for predicting an interaction between the cardiac implant and cardiac region. The interaction can be at least one of mechanical interaction, such as contact pressure, strain, contact area; leakage; regurgitation; cardiac conduction abnormalities; risk of implant misplacement; or the like.

The predicting unit 140 can includes a querying unit 122 arranged for querying a database 124 as can be seen in FIG. 4. The database 124 includes a plurality of records 126. Each record 126 includes data representative of a three-dimensional image of a cardiac region an associated size, and optionally type, of a cardiac implant, and an interaction. The querying unit 122 is arranged for querying the database 124 for determining the record 126 including data representative of a three-dimensional image of a cardiac region and size, and optionally type, of cardiac implant that closest matches the data 4 representative of a patient-specific three-dimensional image of a cardiac region as obtained by the first receiving unit and an intended cardiac implant. Once this closest matching record has been found, the querying unit 122 extracts from this record the data representative of the interaction. The processor 2 uses this data as the prediction for the interaction between the intended cardiac implant and cardiac region of the patient under study.

The predicting unit 140 can include a determination unit 128 arranged for determining, on the basis of the data 4 representative of a patient-specific three-dimensional image of a cardiac region and the size, and optionally type, of the intended cardiac implant, parameter values for a first parametric model, providing a model representation of the patient-specific cardiac region and implant combination, as can be seen in FIG. 5. The predicting unit 140 includes a modelling unit 130. The modelling unit 130 includes a third parametric model. The third parametric model takes the parameter values of the first parametric model to predict the interaction between the intended cardiac implant and cardiac region of the patient under study.

The predicting unit 140 includes an artificial intelligence device 132 as can be seen in FIG. 6. The processing unit 2 is arranged for entering the data representative of the patient-specific three-dimensional image of the cardiac region and the size, and optionally type, of the intended cardiac implant into the artificial intelligence device 132. The artificial intelligence device 132 is arranged for outputting the prediction of the interaction between the intended cardiac implant and cardiac region of the patient under study.

The prediction of the interaction between the intended cardiac implant and cardiac region of the patient under study is a measure for the estimated a risk of complications arising in or after structural heart intervention. The interaction and/or the measure for the estimated risk can be made knowable to the user, e.g. via the user interface, and/or via a communications unit 127, such as a messaging unit, e.g. an email unit.

It will be appreciated that the systems as described in relation to FIGS. 4, 5 and 6 can be combined.

It will be appreciated that the systems of FIGS. 4, 5 and 6 can be used in preoperative planning. It will be appreciated that the data representative of the cardiac implants can relate to different cardiac implants. Each implant can represent geometrical and/or material properties of a cardiac implant. The implants may e.g. differ in size, brand, construction, material or the like. The measure of the risk of the patient developing complications can be determined for each of the implants. From this analysis it can be determined which one of the plurality of implants has associated therewith the lowest risk of the patient developing complications. A cardiac implant corresponding to the implant having the lowest associated risk of the patient developing complications can then be selected for a real-life percutaneous implantation procedure.

The systems 1, 101 as described in view of FIGS. 1-6 can also be used for planning structural heart intervention. The first receiving unit 6, 106 can obtain data representative of a patient-specific three-dimensional image of a cardiac region. The second receiving unit 14, 114 can obtain data representative of a cardiac implant, such as size and optionally type, to be implanted in the cardiac region of the patient. The systems 1, 101 can predict a deployed shape of the cardiac implant in the cardiac region, e.g. as a result of cardiac implant deployment and deformation of the cardiac region. The querying unit 22, 122 can querying a database 24 including a plurality of records 26, each record including data representative of a three-dimensional image of a cardiac region, a cardiac implant, and an a deployed shape of the cardiac implant. The determination unit 28, 128 can determine parameter values for a parametric model representation of the patient-specific cardiac region and implant combination and the modelling unit 30, 130 can use the parameter values in a third parametric model predicting the deployed shape of the cardiac implant. The data representative of the patient-specific three-dimensional image of the cardiac region and the cardiac implant can be entered into the artificial intelligence device 32, 132 which can be arranged for outputting the prediction of the deployed shape of the cardiac implant. The prediction of the deployed shape can be presented to a user by the communications unit 27, 127, e.g. as an overlay on, e.g. a view of, the patient-specific three-dimensional image of the cardiac region, Optionally, in the system 1, 101 includes a checking unit 40, 140 arranged for checking whether the database includes a record matching the patient-specific data better than a predetermined similarity threshold. The system 1, 101 can also include a calculation unit 42, 142, arranged for if no such record is found, calculating the deployed shape of the cardiac implant in the patient-specific cardiac region. The calculating can include obtaining a patient-specific three-dimensional anatomical model representing the patient-specific cardiac region on the basis of the data representative of the patient-specific three-dimensional image of the cardiac region, said patient-specific anatomical model comprising a finite element mesh. The calculating can include obtaining an implant models representing a finite element representation of the cardiac implant. The calculating can include virtually deploying said implant model into said patient-specific anatomical model. The calculating can include calculating a deployed shape of the cardiac implant, optionally at a plurality of deployment locations of the implant model.

The systems 1, 101 as described in view of FIGS. 1-6 can also be used for determining a neo-LVOT area. The first receiving unit 6, 106 can obtain data representative of a patient-specific three-dimensional image of a cardiac region. The second receiving unit 14, 114 can obtain data representative of a mitral valve implant, such as a size and optionally type, to be implanted in the mitral valve annulus region of the patient. The system 1, 101 can predict a deployed shape of the mitral valve implant in the mitral valve annulus region, e.g. as a result of mitral valve implant deployment and deformation of the mitral valve annulus region. The querying unit 22, 122 can query a database 24 including a plurality of records 26, each record including data representative of a three-dimensional image of a mitral valve annulus region, and an associated deployed shape of the mitral valve implant. The determination unit 28, 128 can determine parameter values for a parametric model representation of the patient-specific mitral valve annulus region and mitral valve implant combination and the modelling unit 30, 130 can use the parameter values in a third parametric model for predicting the deployed mitral valve implant shape. The data representative of the patient-specific three-dimensional image of the mitral valve annulus region and of the mitral valve implant can be entered into the artificial intelligence device 32, 132 which can be arranged for outputting the prediction of the deployed shape of the mitral valve implant. The prediction of the deployed shape can be presented to a user by the communication unit 27, 127, e.g. as an overlay on, e.g. a view of, the patient-specific three-dimensional image of the mitral valve annulus region. The method can include a neo-LVOT unit 44, 144 arranged for determining the neo-LVOT area from the patient-specific three-dimensional image of the mitral valve annulus region and the predicted deployed shape of the mitral valve implant, e.g. from the overlay of the predicted deployed shape of the mitral valve implant on, e.g. a view of, the patient-specific three-dimensional image of the mitral valve annulus region.

Optionally, in the system 1, 101 includes a checking unit 40, 140 arranged for checking whether the database includes a record matching the patient-specific data better than a predetermined similarity threshold. The system 1, 101 can also include a calculation unit 42, 142, arranged for if no such record is found, calculating the deployed shape of the cardiac implant in the patient-specific cardiac region.

The calculating can include obtaining a patient-specific three-dimensional anatomical model representing the patient-specific mitral valve annulus region on the basis of the data representative of the patient-specific three-dimensional image of the mitral valve annulus region, said patient-specific anatomical model comprising a finite element mesh. The calculating can include obtaining a mitral valve implant model, representing a finite element representation of the mitral valve implant. The calculating can include virtually deploying said mitral valve implant model into said patient-specific anatomical model. The calculating can include calculating an interaction between the deployed mitral valve implant models and the patient-specific anatomical model. The calculating can include determining the deployed shape, and optionally position, of the mitral valve implant on the basis of the calculated interaction.

A record can be generated including data representative of the three-dimensional image of the cardiac region and the associated deployed shape of the cardiac implant in the cardiac region. The record can be stored in the database 24.

In view of the systems 1 and 101 as described in view of FIGS. 1-6, it will be appreciated that the processor 2, 102 can be included by a network server arranged for receiving the data representative of the patient-specific three-dimensional image of the cardiac region via the network from a user device, and for transmitting data representative of the determined size or interaction and/or risk to the user device.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

It will be appreciated that the processor can be embodied as dedicated electronic circuits, possibly including software code portions. The processor can also be embodied as software code portions executed on, and e.g. stored in, a memory of, a programmable apparatus such as a computer, tablet or smartphone.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier may be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means, e.g. via the internet or cloud.

When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference sign placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:
1. A computer implemented method for selecting, from a series of cardiac implants having different sizes, a cardiac implant having an optimum size, and predicting an optimum deployment position, for implantation of the cardiac implant in a patient, the method comprising:

obtaining a patient-specific three-dimensional anatomical model corresponding to data representative of a patient-specific three-dimensional image of a cardiac region, the patient-specific three-dimensional anatomical model comprising a finite element mesh;

obtaining an implant model representing a finite element representation of the cardiac implant;

virtually deploying the implant model into the patient-specific three-dimensional anatomical model;

calculating a deployed shape of the implant model at a plurality of deployment locations of the implant model; and predicting the optimum size, and optimum position, of the cardiac implant when deployed in the cardiac region based on the patient-specific three-dimensional anatomical model and the implant model, wherein the predicting comprises querying a database including a plurality of records, each record including data representative of a patient-specific three-dimensional image of a cardiac region and an associated size and associated position of the cardiac implant of the series.

2. The method of claim 1, wherein the database includes records associated with respective patient-specific clinical data, and/or records associated with simulated data.

3. The method of claim 1, wherein the database includes records obtained by applying augmentation techniques to other records, the augmentation techniques comprising scaling and/or modifying a histogram.

4. The method of claim 1, wherein the querying of the database includes using extreme gradient boosting.

5. The method of claim 1, wherein the predicting is further based on metadata with respect to the patient, the meta data comprising one or more of demographic data, known pathology, or medicament use.

6. The method of claim 1, wherein a predefined criterion is a lowest risk of complications during and/or after deployment of an actual implant in an actual cardiac region of the patient.

7. A computer implemented method for estimating a risk of complications arising in and/or after structural heart intervention, the method comprising:

obtaining a patient-specific three-dimensional anatomical model corresponding to data representative of a patient-specific three-dimensional image of a cardiac region, the patient-specific three-dimensional anatomical model comprising a finite element mesh;

obtaining data representative of a size and type of a cardiac implant to be implanted in the cardiac region of the patient;

obtaining an implant model representing a finite element representation of the cardiac implant;

virtually deploying the implant model into the patient-specific three-dimensional anatomical model;

calculating a deployed shape of the implant model at a plurality of deployment locations of the implant model; and predicting an interaction between the cardiac implant and cardiac region based on the patient-specific three-dimensional anatomical model and the implant model, wherein the predicting comprises querying a database including a plurality of records, each record including data representative of a patient-specific three-dimensional image of a cardiac region, the size and type of the cardiac implant, and the interaction.

8. The method of claim 7, wherein the interaction is at least one of mechanical interaction leakage, regurgitation, cardiac conduction abnormalities, or risk of implant misplacement.

9. The method of claim 1, including:

using a neural network for generating the plurality of records; and storing the plurality of records in a database.

10. A computer implemented method for planning structural heart intervention, the method comprising:

obtaining a patient-specific three-dimensional anatomic model corresponding to data representative of a patient-specific three-dimensional image of a cardiac region, the patient-specific three-dimensional anatomic model comprising a finite element mesh;

obtaining data representative of a cardiac implant and corresponding to a size and type of the cardiac implant, the cardiac implant configured to be implanted in the cardiac region of the patient;

obtaining an implant model representing a finite element representation of the cardiac implant;

virtually deploying the implant model into the patient-specific three-dimensional anatomical model; and predicting a deployed shape of the cardiac implant in the cardiac region based on the implant model and the patient-specific three-dimensional anatomical model, wherein the predicting comprises querying a database including a plurality of records, each record including data representative of a patient-specific three-dimensional image of a cardiac region, a cardiac implant, and the predicted deployed shape of the cardiac implant in the respective cardiac region.

11. The method of claim 10, wherein the prediction of the deployed shape is presented to a user as an overlay on, a view of the patient-specific three-dimensional image of the cardiac region.

12. The method of claim 10, further comprising determining a neo-LVOT area;

wherein the obtaining data representative of a cardiac implant includes obtaining data representative of a mitral valve implant.

13. The method of claim 12, wherein the prediction of the deployed shape is presented to a user, as an overlay on, a view of the patient-specific three-dimensional image of the cardiac region corresponding to a mitral valve annulus region.

14. The method of claim 5, wherein the neo-LVOT area is determined from the patient-specific three-dimensional image of the cardiac region corresponding to the mitral valve annulus region and the predicted deployed shape.

15. The method of claim 2, further comprising calculating an interaction between the implant model and the patient-specific three-dimensional anatomical model based on the predicted deployed shape.

* * * * *